(12) United States Patent
Capelli et al.

(10) Patent No.: US 10,835,767 B2
(45) Date of Patent: Nov. 17, 2020

(54) RAPID PULSE ELECTROHYDRAULIC (EH) SHOCKWAVE GENERATOR APPARATUS AND METHODS FOR MEDICAL AND COSMETIC TREATMENTS

(71) Applicants: Soliton, Inc., Houston, TX (US); Board of Regents, The University of Texas System, Austin, TX (US)

(72) Inventors: Christopher C. Capelli, Houston, TX (US); Robert Crowley, Sudbury, MA (US)

(73) Assignees: BOARD OF REGENTS, THE UNIVERSITY OF TEXAS SYSTEM, Austin, TX (US); SOLITON, INC., Houston, TX (US)

( * ) Notice: Subject to any disclaimer, the term of this patent is extended or adjusted under 35 U.S.C. 154(b) by 56 days.

(21) Appl. No.: 13/798,710

(22) Filed: Mar. 13, 2013

(65) Prior Publication Data

US 2014/0257144 A1    Sep. 11, 2014

Related U.S. Application Data

(60) Provisional application No. 61/775,232, filed on Mar. 8, 2013.

(51) Int. Cl.
*A61N 7/00* (2006.01)
*A61B 17/225* (2006.01)
(Continued)

(52) U.S. Cl.
CPC .............. *A61N 7/00* (2013.01); *A61B 17/225* (2013.01); *A61B 17/2251* (2013.01);
(Continued)

(58) Field of Classification Search
CPC .... A61B 2019/5219; A61B 17/320068; A61N 2007/0034; A61N 7/00; A61N 2007/0008;
(Continued)

(56) References Cited

U.S. PATENT DOCUMENTS 3,613,069 A    10/1971  Cary .............................. 367/92
3,735,764 A *  5/1973  Balev ..................... G10K 15/06
                                                                601/4
(Continued)

FOREIGN PATENT DOCUMENTS

CN          101155614         4/2008
CN          101610736        12/2009
(Continued)

OTHER PUBLICATIONS

Baumler et al., Q-Switch Laser and Tattoo Pigments: First Results of the Chemical and Photophysical Analysis of 41 Compounds, Lasers in Surgery and medicine 26:13-21 (2000), pp. 13-21.
(Continued)

*Primary Examiner* — Amelie R Davis
(74) *Attorney, Agent, or Firm* — Norton Rose Fulbright US LLP

(57) ABSTRACT

Apparatuses and methods for electrohydraulic generation of shockwaves at a rate of between 10 Hz and 5 MHz, and/or that permit a user to view a region of a patient comprising target cells during application of generated shockwaves to the region. Methods of applying electro-hydraulically generated shockwaves to target tissues (e.g., for reducing the appearance of tattoos, treatment or reduction of certain conditions and/or maladies).

25 Claims, 12 Drawing Sheets

(51) Int. Cl.
| | |
|---|---|
| *G10K 15/04* | (2006.01) |
| *G10K 11/26* | (2006.01) |
| *A61H 23/00* | (2006.01) |
| *A61B 17/22* | (2006.01) |
| *A61H 23/02* | (2006.01) |
| *A61B 17/00* | (2006.01) |
| *A61B 90/00* | (2016.01) |

(52) U.S. Cl.
CPC ........... *A61H 23/008* (2013.01); *G10K 11/26* (2013.01); *G10K 15/043* (2013.01); *A61B 2017/00769* (2013.01); *A61B 2017/22024* (2013.01); *A61B 2090/3616* (2016.02); *A61H 23/0236* (2013.01); *A61H 2201/0153* (2013.01); *A61H 2201/10* (2013.01); *A61H 2201/105* (2013.01); *A61H 2201/1207* (2013.01); *A61H 2201/1238* (2013.01); *A61H 2201/1635* (2013.01); *A61H 2201/5005* (2013.01); *A61N 2007/0034* (2013.01)

(58) Field of Classification Search
CPC .... A61N 2007/0013; A61H 2201/0153; A61H 2201/10; A61H 2201/105; A61H 2201/1207; A61H 2201/1238; A61H 2201/1635; A61H 2201/5005; A61H 23/008; A61H 23/0236; G10K 11/26; G10K 15/043
See application file for complete search history.

(56) References Cited

U.S. PATENT DOCUMENTS

| | | | |
|---|---|---|---|
| 3,769,963 A * | 11/1973 | Goldman et al. ............... 600/476 |
| 3,942,531 A * | 3/1976 | Hoff ..................... G10K 15/043 |
| | | | 601/4 |
| 4,311,147 A * | 1/1982 | Hausler ............................ 601/4 |
| 4,715,376 A | 12/1987 | Nowacki et al. |
| 4,858,597 A * | 8/1989 | Kurtze .................... G10K 11/32 |
| | | | 601/4 |
| 4,896,673 A | 1/1990 | Rose et al. .................... 600/439 |
| 4,905,671 A * | 3/1990 | Senge ............... A61B 17/22004 |
| | | | 601/4 |
| 4,962,752 A | 10/1990 | Reichenberger et al. ........ 601/4 |
| 4,979,501 A | 12/1990 | Valchanov et al. .............. 601/2 |
| 5,009,232 A * | 4/1991 | Hassler ............. A61B 17/2256 |
| | | | 600/439 |
| 5,015,929 A | 5/1991 | Cathignol et al. ............ 310/335 |
| 5,149,406 A | 9/1992 | Mullen et al. |
| 5,150,713 A | 9/1992 | Okazaki ....................... 600/439 |
| 5,193,527 A | 3/1993 | Schafer .............................. 601/2 |
| 5,195,508 A | 3/1993 | Muller et al. .................... 601/4 |
| 5,204,820 A | 4/1993 | Strobel et al. |
| 5,231,976 A * | 8/1993 | Wiksell ............. A61B 17/22004 |
| | | | 181/113 |
| 5,240,005 A | 8/1993 | Viebach ........................ 600/472 |
| 5,259,368 A * | 11/1993 | Wiksell ................... G10K 15/06 |
| | | | 367/147 |
| 5,284,143 A | 2/1994 | Rattner .......................... 600/427 |
| 5,304,170 A | 4/1994 | Green |
| 5,304,207 A * | 4/1994 | Stromer ..................... A61N 1/32 |
| | | | 607/145 |
| 5,327,890 A | 7/1994 | Matura et al. ................. 600/427 |
| 5,360,447 A | 11/1994 | Koop |
| 5,374,236 A * | 12/1994 | Hassler ............................ 601/2 |
| 5,393,296 A | 2/1995 | Rattner ............................ 601/2 |
| 5,409,446 A | 4/1995 | Rattner ............................ 601/4 |
| 5,419,327 A | 5/1995 | Rohwedder et al. ......... 600/439 |
| 5,423,803 A | 6/1995 | Tankovich et al. |
| 5,435,304 A | 7/1995 | Oppelt et al. ................. 600/439 |
| 5,458,652 A | 10/1995 | Uebelacker ....................... 604/4 |
| 5,529,572 A | 6/1996 | Spector |
| 5,595,178 A | 1/1997 | Voss et al. ..................... 600/427 |
| 5,618,275 A | 4/1997 | Bock .............................. 604/290 |
| 5,658,239 A | 8/1997 | Delmenico |
| 5,675,495 A | 10/1997 | Biermann et al. |
| 5,676,159 A | 10/1997 | Navis ............................ 128/846 |
| 5,709,676 A | 1/1998 | Alt |
| 5,722,411 A * | 3/1998 | Suzuki ..................... A61N 7/02 |
| | | | 600/439 |
| 5,790,305 A | 8/1998 | Marcellin-Dibon et al. |
| 5,827,204 A | 10/1998 | Grandia et al. .................... 601/2 |
| 6,013,122 A | 1/2000 | Klitzman et al. ........... 106/31.03 |
| 6,036,661 A | 3/2000 | Schwarze et al. ............... 601/4 |
| 6,039,694 A | 3/2000 | Larson et al. |
| 6,058,932 A * | 5/2000 | Hughes .............. A61H 23/0236 |
| | | | 128/200.24 |
| 6,080,119 A | 6/2000 | Schwarze et al. ............... 601/4 |
| 6,096,029 A | 8/2000 | O'Donnell, Jr. .................. 606/9 |
| 6,113,559 A | 9/2000 | Klopotek ......................... 601/3 |
| 6,113,560 A | 9/2000 | Simnacher ....................... 601/4 |
| 6,176,839 B1 | 1/2001 | Deluis et al. ...................... 601/2 |
| 6,186,963 B1 | 2/2001 | Schwarze et al. ............... 601/2 |
| 6,210,329 B1 | 4/2001 | Christmas et al. |
| 6,309,355 B1 | 10/2001 | Cain et al. .................... 600/439 |
| 6,325,769 B1 | 12/2001 | Klopotek |
| 6,350,245 B1 | 2/2002 | Cimino ............................ 601/2 |
| 6,368,929 B1 | 4/2002 | Hill et al. ..................... 438/312 |
| 6,390,995 B1 | 5/2002 | Ogden et al. ..................... 601/1 |
| 6,450,979 B1 | 9/2002 | Miwa et al. |
| 6,454,713 B1 | 9/2002 | Ishibashi et al. ............. 600/439 |
| 6,487,447 B1 | 11/2002 | Weimann et al. .............. 604/20 |
| 6,491,685 B2 | 12/2002 | Visuri ........................... 606/2.5 |
| 6,519,376 B2 | 2/2003 | Biagi et al. ....................... 385/7 |
| 6,551,308 B1 | 4/2003 | Muller et al. |
| 6,666,834 B2 | 12/2003 | Resile et al. ..................... 601/2 |
| 6,755,821 B1 | 6/2004 | Fry ................................ 606/15 |
| 6,800,122 B2 | 10/2004 | Anderson et al. .......... 106/31.03 |
| 6,905,467 B2 | 6/2005 | Bradley ....................... 600/443 |
| 6,942,663 B2 | 9/2005 | Vargas et al. |
| 6,948,843 B2 | 9/2005 | Laugharn et al. ............ 366/127 |
| 6,972,116 B2 | 12/2005 | Brill et al. ................. 422/186.04 |
| 7,189,209 B1 | 3/2007 | Ogden et al. |
| 7,250,047 B2 | 7/2007 | Anderson et al. .............. 606/32 |
| 7,311,678 B2 | 12/2007 | Spector ............................. 601/2 |
| 7,364,554 B2 | 4/2008 | Bolze et al. ...................... 601/2 |
| 7,405,510 B2 | 6/2008 | Kaminski et al. ............. 310/334 |
| 7,470,240 B2 | 12/2008 | Schultheiss et al. ............. 601/2 |
| 7,507,213 B2 | 3/2009 | Schultheiss et al. ............. 601/2 |
| 7,588,547 B2 | 9/2009 | Deem et al. |
| 7,867,178 B2 | 1/2011 | Simnacher ....................... 601/2 |
| 7,985,189 B1 | 7/2011 | Ogden et al. ..................... 601/2 |
| 7,988,631 B2 | 8/2011 | Bohris .......................... 600/439 |
| 8,057,408 B2 | 11/2011 | Cain et al. ........................ 601/2 |
| 8,088,073 B2 | 1/2012 | Simnacher et al. |
| 8,092,401 B2 | 1/2012 | Schultheiss ....................... 601/2 |
| 8,102,734 B2 | 1/2012 | Sliwa et al. ................... 367/140 |
| 8,235,899 B2 | 8/2012 | Hashiba ........................ 600/437 |
| 8,257,282 B2 | 9/2012 | Uebelacker et al. ............. 601/4 |
| 8,298,162 B2 | 10/2012 | Del Giglio |
| 8,323,220 B2 | 12/2012 | Babaev |
| 8,343,420 B2 | 1/2013 | Cioanta et al. .................. 422/20 |
| 8,357,095 B2 | 1/2013 | Anderson et al. ............ 600/441 |
| 8,684,970 B1 * | 4/2014 | Koyfman ............. A61B 17/2251 |
| | | | 604/140 |
| 2002/0009015 A1 | 1/2002 | Laugharn et al. ............. 366/108 |
| 2002/0193831 A1 | 12/2002 | Smith |
| 2003/0233045 A1 | 12/2003 | Vaezy |
| 2004/0006288 A1 | 1/2004 | Spector et al. |
| 2004/0181219 A1 | 9/2004 | Goble et al. |
| 2005/0015023 A1 | 1/2005 | Ein-Gal |
| 2005/0150830 A1 | 7/2005 | Laugharn et al. |
| 2006/0036168 A1 | 2/2006 | Liang et al. |
| 2006/0064082 A1 * | 3/2006 | Bonutti .................... A61N 7/00 |
| | | | 606/32 |
| 2006/0173388 A1 | 8/2006 | Ginter et al. |
| 2006/0184071 A1 | 8/2006 | Klopotek |
| 2006/0200116 A1 | 9/2006 | Ferren et al. |
| 2007/0016112 A1 | 1/2007 | Schultheiss et al. |
| 2007/0038060 A1 | 2/2007 | Cerwin et al. ................. 600/407 |
| 2007/0049829 A1 | 3/2007 | Kaminski et al. ............ 600/459 |
| 2007/0055180 A1 | 3/2007 | Deem |

(56) References Cited

U.S. PATENT DOCUMENTS

| | | |
|---|---|---|
| 2007/0065420 A1 | 3/2007 | Johnson |
| 2007/0219760 A1 | 9/2007 | Yang et al. |
| 2007/0239072 A1 | 10/2007 | Schultheiss et al. |
| 2007/0239082 A1* | 10/2007 | Schultheiss ...... A61B 17/22004 601/4 |
| 2007/0239084 A1* | 10/2007 | Voss ...................... A61H 23/008 601/4 |
| 2007/0249939 A1 | 10/2007 | Gerbi et al. ................... 600/462 |
| 2008/0009774 A1 | 1/2008 | Capelli et al. ..................... 601/3 |
| 2008/0009885 A1 | 1/2008 | Del Giglio ......................... 606/128 |
| 2008/0021447 A1 | 1/2008 | Davison et al. |
| 2008/0071198 A1* | 3/2008 | Ogden et al. ...................... 601/2 |
| 2008/0107744 A1 | 5/2008 | Chu .............................. 424/489 |
| 2008/0132810 A1 | 6/2008 | Scoseria et al. .................... 601/4 |
| 2008/0146971 A1 | 6/2008 | Uebelacker et al. ............. 601/4 |
| 2008/0154157 A1 | 6/2008 | Altshuler et al. |
| 2008/0183200 A1 | 7/2008 | Babaev .......................... 606/169 |
| 2008/0194967 A1 | 8/2008 | Sliwa et al. ..................... 600/472 |
| 2008/0195003 A1 | 8/2008 | Sliwa et al. ......................... 601/3 |
| 2008/0262483 A1* | 10/2008 | Capelli ..................... A61N 7/02 606/9 |
| 2008/0269163 A1 | 10/2008 | Sostaric et al. |
| 2008/0269608 A1 | 10/2008 | Anderson et al. ............ 600/439 |
| 2008/0319356 A1* | 12/2008 | Cain et al. ......................... 601/2 |
| 2009/0018472 A1 | 1/2009 | Soltani et al. |
| 2009/0275832 A1 | 11/2009 | Gelbart et al. |
| 2010/0076349 A1 | 3/2010 | Babaev .............................. 601/2 |
| 2010/0082019 A1 | 4/2010 | Neev |
| 2010/0087899 A1 | 4/2010 | Erez et al. .................... 607/101 |
| 2010/0168575 A1 | 7/2010 | Hashiba ........................ 600/443 |
| 2010/0204617 A1 | 8/2010 | Ben-Ezra |
| 2010/0208467 A1 | 8/2010 | Dross |
| 2010/0274161 A1 | 10/2010 | Azhari et al. |
| 2010/0280420 A1* | 11/2010 | Barthe et al. ...................... 601/2 |
| 2010/0331741 A9 | 12/2010 | Cioanta et al. ................... 601/2 |
| 2011/0034832 A1 | 2/2011 | Cioanta et al. ................... 601/1 |
| 2011/0087157 A1 | 4/2011 | Cioanta et al. ................. 604/22 |
| 2012/0157892 A1 | 6/2012 | Reitmajer et al. |
| 2012/0253240 A1 | 10/2012 | Uebelacker et al. |
| 2012/0253416 A1 | 10/2012 | Erez et al. ......................... 607/3 |
| 2012/0310232 A1 | 12/2012 | Erez ................................ 606/33 |
| 2012/0323147 A1 | 12/2012 | Scheirer .......................... 601/2 |
| 2012/0330288 A1 | 12/2012 | Clementi et al. |
| 2013/0018287 A1 | 1/2013 | Capelli ............................. 601/2 |
| 2013/0046179 A1 | 2/2013 | Humayun |
| 2013/0046207 A1 | 2/2013 | Capelli |
| 2014/0005576 A1* | 1/2014 | Adams ............. A61B 17/22022 601/4 |
| 2014/0243715 A1 | 8/2014 | Cioanta et al. |
| 2014/0257144 A1 | 9/2014 | Capelli et al. |
| 2014/0276722 A1 | 9/2014 | Parihar et al. |
| 2014/0277219 A1 | 9/2014 | Nanda |
| 2015/0126913 A1 | 5/2015 | Jurna et al. |
| 2016/0016013 A1 | 1/2016 | Capelli et al. |
| 2016/0067139 A1 | 3/2016 | Katragadda et al. |

FOREIGN PATENT DOCUMENTS

| | | |
|---|---|---|
| CN | 102057422 | 5/2011 |
| CN | 102247661 | 11/2011 |
| CN | 105246419 | 1/2016 |
| CN | 105209117 | 12/2016 |
| EP | 0243650 | 11/1987 |
| EP | 0322473 | 7/1989 |
| EP | 0326620 | 8/1989 |
| EP | 2964326 | 1/2016 |
| EP | 3626307 | 3/2020 |
| JP | S61-293447 | 12/1986 |
| JP | 62-192150 | 8/1987 |
| JP | S63-183050 | 7/1988 |
| JP | 6-7365 | 1/1994 |
| JP | H06-505648 | 6/1994 |
| JP | 8-140984 | 6/1996 |
| JP | 8-194079 | 7/1996 |
| JP | 9-103434 | 4/1997 |
| JP | 2007-000218 | 1/2007 |
| JP | 2009-518126 | 4/2009 |
| RU | 2121812 C1 | 11/1998 |
| RU | 2151559 C1 | 6/2000 |
| TW | I292341 | 1/2008 |
| TW | I350249 | 10/2011 |
| WO | WO 02/030256 A2 | 4/2002 |
| WO | WO 2007/067563 | 6/2007 |
| WO | WO/07/146988 | 12/2007 |
| WO | WO 2008/052198 | 5/2008 |
| WO | WO 2008/074005 | 6/2008 |
| WO | WO 2008/137942 | 11/2008 |
| WO | WO 11/0077466 A1 | 6/2011 |
| WO | 2011/091020 * | 7/2011 |
| WO | WO/11/091020 | 7/2011 |
| WO | WO 2013/012724 | 1/2013 |
| WO | WO 2014/138582 | 9/2014 |
| WO | WO 2014/191263 | 12/2014 |

OTHER PUBLICATIONS

Chen et al., "The disappearance of ultrasound contrast bubbles: Observations of bubble dissolution and Cavitation nucleation", Ultrasound in Med. & Biol., vol. 28, No. 6, pp. 793-803, 2002.

Eisenmenger, W. et al., "The First Clinical Results of Wide-Focus and Low-Pressure ESWL" Ultrasound in Med. & Biol., vol. 28, No. 6, pp. 769-774, 2002.

Eisenmenger, Wolfgang, "The Mechanisms of Stone Fragmentation in ESWL", Ultrasound in Med. & Biol., vol. 27, No. 5, pp. 683-693, 2001.

Ho et al., "Laser-Tattoo Removal—A Study of the Mechanism and the Optimal Treatment Strategy via Computer Simulations", Lasers in Surgery and medicine 30:389-391 (2002).

International Preliminary Report on Patentability of PCT/US2011/021692, dated Jul. 24, 2012, 6 pages.

Kuhn et al., "Impact of extracorporeal shock waves on the human skin with cellulite: A case study of an unique instance", Clinical Interventions of Aging, 3(1):201-210, 2008.

Kuperman-Beade et al., "Laser Removal of Tattoos", Am J Clin Dermatol 2001: 2(1):21-25.

Kuzmin et al., "Ultrasonic Cavitational Chemical Technologies", XI Session of the Russian Acoustical Society, Moscow, Nov. 19-23, 2001.

Ng et al., "Therapeutic Ultrasound: Its Application in Drug Delivery", Medicinal Research Reviews, vol. 22, No. 2, 204-223, 2002.

Notice of Allowance in Canadian Application No. 2,787,528 dated Apr. 9, 2014.

Notice of Final Rejection in Korean Application No. 10-2012-7021437 dated Jun. 26, 2014.

Notice of Preliminary Rejection in Korean Application No. 10-2012-7021437 dated Oct. 24, 2013.

Office Action in Japanese Patent Application No. 2012-550085 dated Oct. 2, 2014.

Office Communication in Chinese Application No. 201180011442.0 dated Jul. 3, 2014.

Ogden et al., Principles of Shock Wave Therapy, Clinical Orthopaedics and Related Research, No. 387, pp. 8-17.

Patent Examination Report No. 1 in Australian Patent Application No. 2012284323 dated Jan. 9, 2014.

Ross et al., "Comparison of Responses of Tattoos to Picosecond and Nanosecond Q-Switched Neodymium: YAG Lasers" ARCH Dermatol/ vol. 134, Feb. 1998, pp. 167-171.

Search Report and Written Opinion issued in PCT/US2011/021692, dated Sep. 20, 2011.

Search Report and Written Opinion issued in PCT/US2012/046674, dated Oct. 26, 2012.

Search Report and Written Opinion issued in PCT/US2014/021746, dated Sep. 12, 2014.

Sheth and Pandya, "Melsama: A comprehensive update (Part I)", Journal of the American Academy of Dermatology, 65:689-697, 2011.

(56) References Cited

OTHER PUBLICATIONS

Sheth and Pandya, "Melsama: A comprehensive update (Part II)", *Journal of the American Academy of Dermatology*, 65:699-714, 2011.
Solis et al., "Experimental Nonsurgical Tattoo Removal in a Guinea Pig Model with Topical Imiquimod and Tretinoin", Dermatol Surg. 2002, 28:83-87.
Timko et al., "In Vitro Quantitative Chemical Analysis of Tattoo Pigments", ARCH Dermatol/vol. 137, Feb. 2001, pp. 143-147.
Varma, S., "Tattoo Ink Darkening of a yellow Tattoo after Q-Switched Laser Treatment", 2002 Blackwell Science Ltd., Clinical and Experimental Dermatology, 27, 461-463.
Wolfrum et al., "Shock wave induced interaction of microbubbles and boundaries", Physics of Fluids, vol. 15, No. 10, Oct. 2003, pp. 2916-2922.
European Search Report in European Application No. EP 14760628 dated Sep. 23, 2016.
International Preliminary Report on Patentability in International Application No. PCT/US2014/021746 dated Sep. 17, 2015.
Office Action issued in Chinese Patent Application No. 201480023497.7, dated Jan. 16, 2019.
Notice of Reasons for Rejection issued in Japanese Patent Application No. 2015-561713, dated Oct. 23, 2017 (English Translation).
Office Action issued in Taiwanese Application No. 103108904, dated May 2, 2018.
Bickle, Abdominal X Rays Made Easy: Calcification, Student BMJ vol. 10, Aug. 2002, 272-274.
Decision on Grant Patent for Invention in Russian Application No. 2012135506/14(057136) dated May 12, 2014.
Delius, et al., "Biological Effects of Shock Waves: Kidney Haemorrhage by Shock Waves in Dogs—Administration Rate Dependence," *Ultrasound Med Biol.*, 14(8), 689-694, 1988.
Examination Search Report Issued in Canadian Patent Application No. 2,904,394 , dated Apr. 7, 2020.
Extended European Search Report Issued in Corresponding European Patent Application No. 19187877.6, dated Feb. 18, 2020.
Falco, "Single-Point Nonlinearity Indicators for the Propagation of High Amplitude Acoustic Signals," Ph.D. Thesis. Graduate Program in Acoustics, the Pennsylvania State University, University Park, Pa, May 2007.
Fernando, "A Nonlinear Computational Method for the Propagation of Shock Waves in Aero-Engine Inlets Towards a New Model for Buzz-Saw Noise Prediction," 15th AIAA/CEAS Aerocoustics Conference (30th Aerocoustics Conference) May 11-13, 2009, 1-18.
Gillitzer, et al., "Low-Frequency Extracorporeal Shock Wave Lithotripsy Improves Renal Pelvic Stone Disintegration an a Pig Model," *BJU Int*, 176, 1284-1288, 2009.
International Preliminary Report on Patentability issued in Application No. PCT/US2017/023728, dated Sep. 25, 2018.
Liu, et al., "Optimized Design of LED Freeform Lens for Uniform Circular Illumination," Journal of Zhejiang University-Science C, Computer & Electron, 13(12), 929-936, 2012.
Madbouly, et al., "Slow Versus Fast Shock Wave Lithotripsy Rate for Urolithiasis: A Prospective Randomized Study," The Journal of Urology, 173, 127-130, 2005.
Nana, et al., "Application of the Multiple Low-Energy Q-Switched Laser for the Treatment of Tattoos in 21 Cases," China Aesthetic Medicine, 4(21), 621-622, 2012. (English Abstract).
Office Action issued in Taiwan Application No. 103108084, dated Apr. 27, 2018.
Vogel, et al., "Shock Wave Emission and Cavitation Bubble Generation by Picosecond and Nanosecond Optical Breakdown in Water," J. Acoust. Soc. Am., 100 (1) Jul. 1996.

\* cited by examiner

RAPID PULSE ELECTROHYDRAULIC (EH) SHOCKWAVE GENERATOR APPARATUS AND METHODS FOR MEDICAL AND COSMETIC TREATMENTS

CROSS-REFERENCE TO RELATED APPLICATION

This application claims priority to U.S. Provisional Patent Application No. 61/775,232, filed Mar. 8, 2013, which is incorporated by reference in its entirety.

BACKGROUND

1. Field of the Invention

The present invention relates generally to therapeutic uses for shock waves or shockwaves. More particularly, but not by way of limitation, the present invention relates to an apparatus for generating therapeutic shock waves or shockwaves (shock waves with therapeutic uses).

2. Description of Related Art

Acoustic shockwaves have been used for certain therapies for a number of years. "Shock wave" or "shockwave" is generally used to refer to an acoustic phenomenon (e.g., resulting from an explosion or lightning) that creates a sudden and intense change in pressure. These intense pressure changes can produce strong waves of energy that can travel through elastic media such as air, water, human soft tissue, or certain solid substances such as bone, and/or can induce an inelastic response in such elastic media. Methods for creating shock waves for therapeutic uses include: (1) electrohydraulic, or spark gap (EH); (2) electromagnetic, or EMSE; and (3) piezoelectric. Each is based upon its own unique physical principles.

A. Devices and Systems for Shockwave Generation

U.S. patent application Ser. No. 13/574,228 (a national-stage application of PCT/US2011/021692, which published as WO 2011/091020), by one of the present inventors, discloses a device for producing shock waves at a high pulse rate using a transducer. That device includes an acoustic-wave generator configured to emit acoustic waves having at least one frequency between 1 MHz and 1000 MHz; a shockwave housing coupled to the acoustic-wave generator; and a shockwave medium disposed in the shockwave housing; where the apparatus is configured such that if the acoustic-wave generator emits acoustic waves then at least some portion of the acoustic waves will travel through the shockwave medium and form shock waves. That device can be actuated to form shock waves configured to cause particles within a patient to rupture one or more cells of the patient, and the shock waves can be directed to cells of a patient such that the shock waves cause particles to rupture one or more of the cells. This acoustic-transducer device can produce high powered shockwaves at high frequencies or pulse rates.

Other systems for producing shockwaves can include an electrohydraulic (EH) wave generator. EH systems can generally deliver similar levels of energy as other methods, but may be configured to deliver that energy over a broader area, and therefore deliver a greater amount of shock wave energy to targeted tissue over a shorter period of time. EH systems generally incorporate an electrode (i.e., a spark plug) to initiate a shock wave. In EH systems, high energy shock waves are generated when electricity is applied to an electrode immersed in treated water contained in an enclosure. When the electrical charge is fired, a small amount of water is vaporized at the tip of the electrode and the rapid, nearly instantaneous, expansion of the vaporized water creates a shock wave that propagates outward through the liquid water. In some embodiments, the water is contained in an ellipsoid enclosure. In these embodiments, the shock wave may ricochet from the sides of the ellipsoid enclosure and converge at a focal point that coincides with the location of the area to be treated.

For example, U.S. Pat. No. 7,189,209 (the '209 patent) describes a method of treating pathological conditions associated with bone and musculoskeletal environments and soft tissues by applying acoustic shock waves. The '209 patent describes that shockwaves induce localized trauma and cellular apoptosis therein, including micro-fractures, as well as to induce osteoblastic responses such as cellular recruitment, stimulate formation of molecular bone, cartilage, tendon, fascia, and soft tissue morphogens and growth factors, and to induce vascular neoangiogenesis. The '209 patent claims several specific implementations of its method. For instance, the '209 patent claims a method of treating a diabetic foot ulcer or a pressure sore, comprising: locating a site or suspected site of the diabetic foot ulcer or pressure sore in a human patient; generating acoustic shock waves; focusing the acoustic shock waves throughout the located site; and applying more than 500 to about 2500 acoustic shock waves per treatment to the located site to induce micro-injury and increased vascularization thereby inducing or accelerating healing. The '209 patent discloses a frequency range of approximately 0.5-4 Hz, and application of about 300 to 2500 or about 500 to 8,000 acoustic shock waves per treatment site, which can result in a treatment duration for each treatment site and/or a "total time per treatment" for all sites that is inconveniently large. For example, the '209 patent discloses total times per treatment for different examples ranging from 20 minutes to 3 hours.

U.S. Pat. No. 5,529,572 (the '572 patent) includes another example of the use of electro-hydraulically generated shockwaves to produce therapeutic effect on tissues. The '572 patent describes a method of increasing the density and strength of bone (to treat osteoporosis), comprising subjecting said bone to substantially planar, collimated compressional shock waves having a substantially constant intensity as a function of distance from a shock wave source, and wherein said collimated shock waves are applied to the bone at an intensity of 50-500 atmospheres. The '572 patent describes the application of unfocussed shock waves to produce dynamic repetitive loading of the bone to increase mean bone density, and thereby strengthen bone against fracture. As described in the '572 patent, "the unfocussed shock waves preferably are applied over a relatively large surface of the bone to be treated, for example to cover an area of from 10 to 150 $cm^2$. The intensity of the shock waves may be from 50-500 atmospheres. Each shock wave is of duration of a few microseconds, as in a conventional lithotripter, and is preferably applied at a frequency of 1-10 shock waves per second for a period of 5-30 minutes in each treatment. The number of treatments depends on the particular patient."

U.S. patent application Ser. No. 10/415,293 (the '293 Application), which is also published as US 2004/0006288, discloses another embodiment of the use of EH-generated shockwaves to provide a therapeutic effect on tissues. The '293 Application discloses a device, system, and method for the generation of therapeutic acoustic shock waves for at least partially separating a deposit from a vascular structure. The '293 Application describes that the device can produce shockwaves at a pulse rate of about 50 to about 500 pulses per minute (i.e., 0.83 to 8.33 Hz) with a number of pulses per treatment site (in terms of per length of vascular unit being treated) from about 100 to about 5,000 per 1 $cm^2$.

B. Shockwave Rate

Prior art literature has indicated that faster pulse rates using EH systems to provide shockwaves can lead to tissue damage. For example, in one study (Delius, Jordan, & et al, 1988) [2], the effect of shock waves on normal canine kidneys was examined in groups of dogs whose kidneys were exposed to 3000 shockwaves. The groups differed only in the rate of shockwave administration which was 100 Hz and 1 Hz, respectively. Autopsy was performed 24 to 30 hours later. Macroscopically and histologically, significantly more hemorrhages occurred in kidney parenchyma if shockwaves were administered at a rate of 100 Hz (vs 1 Hz). The results showed that kidney damage is dependent on the rate of shockwave administration.

In another study (Madbouly & et al, 2005) [7], slow shockwave lithotripsy rate (SWL) was associated with a significantly higher success rate at a lower number of total shockwaves compared to the fast shockwave lithotripsy rate. In this paper, the authors discussed how human studies have also shown a decrease in the incidence of SWL induced renal injury or need for anesthesia when slower rates of test SWL were used.

In yet another study (Gillitzer & et al, 2009) [5], slowing the delivery rate from 60 to 30 shockwaves per minute also provides a dramatic protective effect on the integrity of real vasculature in a porcine model. These findings support potential strategies of reduced pulse rate frequency to improve safety and efficacy in extracorporeal shockwave lithotripsy.

C. Tissue as a Viscoelastic Material

One reason for sensitivity to pulse rate found in the prior art may be due in part to the relaxation time of tissue. Cells have both elastic and viscous characteristics, and thus are viscoelastic materials. Unlike most conventional materials, cells are highly nonlinear with their elastic modulus depending on the degree of applied or internal stress. (Kasza, 2007) [6]. One study (Fernandez (2006) [3] suggests that fibroblast cells can be modeled as a gel having a cross-linked actin network that show a transition from a linear regime to power law strain stiffening.

The authors of another paper (Freund, Colonius, & Evan, 2007) [4] hypothesize that the cumulative shear of the many shocks is damaging, and that the mechanism may depend on whether there is sufficient time between shocks for tissue to relax to the unstrained state. Their viscous fluid model suggested that any deformation recovery that will occur is nearly complete by the first 0.15 second after the shock. As a result, their model of the mechanism for cell damage would be independent of shock rate for shock rates slower than ~6 Hz. However, actual viscoelasticity of the interstitial material, with a relaxation time about 1 second, would be expected to introduce its sensitivity to the shock delivery rate. Assuming the interstitial material has a relaxation time of ~1 second, the authors would expect significantly decrease damage for delivery rates lower than ~1 Hz. Conversely, damage should increase for faster delivery rates. Implications of their model are that slowing delivery rates and broadening focal zones should both decrease injury.

SUMMARY

Soft tissues may transition from elastic to viscous behavior for pulse rates (PRs) between 1 Hz and 10 Hz. As a result, potential damage to tissue from shockwaves at PRs between 1 Hz and 10 Hz is unpredictable when typical lithotripsy power levels are used. Perhaps as a result, the prior art teaches slower PRs and large total times per treatment (TTPT). For example, currently known EH shockwave systems generally deliver PRs of less than 10 Hz and require large total times per treatment (TTPT) (e.g., TTPT periods of minutes or even hours for even a single treatment site). When, as may be typical, a treatment requires repositioning of a device at multiple treatment sites, the TTPT becomes large and potentially impractical for many patients and treatment needs.

While long treatment times may be acceptable for extracorporeal shockwave lithotripsy, the use of shockwaves to provide non-lithotripsy therapeutic effects on tissue in the medical setting is less than optimal if not impractical. For example, the cost of treatment often increases with the time needed to administer a treatment (e.g., due to the labor, facilities and other resource costs allocated to the administration of the treatment). Furthermore, in addition to costs, at some point the duration of providing treatment to the patient becomes unbearable for the patient receiving, and healthcare staff providing, the treatment.

This disclosure includes embodiments of apparatuses and methods for electrohydraulic generation of therapeutic shockwaves. The present EH-shockwave systems and methods are configured to deliver shockwaves to tissues to provide a predictable therapeutic effect on the tissue, such as by delivering shockwaves at higher (e.g., greater than ~10 Hz) to reduce TTPT relative to known systems.

The present embodiments of electrohydraulic (EH) apparatuses can be configured to generate high-frequency shock waves in a controlled manner (e.g., using an electrohydraulic spark generator and a capacitive/inductive coil spark generating system). The present pulse-generation (e.g., electrohydraulic spark circuits) can comprise one or more EH tips and, with the present capacitive/inductive coil spark generating systems, can produce a spark pulse rate of 10 Hz to 5 MHz. The shock waves can be configured to impose sufficient mechanical stress to the targeted cells of the tissue to rupture the targeted cells, and can be delivered to certain cellular structures of a patient for use in medical and/or aesthetic therapeutic applications.

The present high-pulse rate (PR) shockwave therapies can be used to provide a predictable therapeutic effect on tissue while having a practical total time per treatment (TTPT) at the treatment site. The present high-PR shockwave therapies can be used to provide a predictable therapeutic effect on tissue, if the viscoelastic nature of the tissue is considered. Specifically, shockwave therapy utilizing a PR greater than 10 Hz and even greater than 100 Hz can be used to provide a predictable therapeutic effect on tissue because at those PRs the tissue is, for the most part, predictably viscous in nature and generally does not vary between elastic and viscous states. Given that tissue behaves as a viscous material at great enough PRs, the PR and power level can be adjusted to account for the tissue's viscous properties. When the viscous nature of the tissue is accounted for using higher PRs, lower power levels can be used to achieve therapeutic effects. One benefit of using higher PRs in combination with lower power levels is the reduction in cavitation formation, which further improves predictability of the present shockwave therapies. Embodiments of the present EH apparatuses and methods can provide targeted rupturing of specific cells without damaging side effects such as cavitation or thermal degradation of surrounding non-targeted cells.

Some embodiments of the present apparatuses (for generating therapeutic shock waves) comprise: a housing defining a chamber and a shockwave outlet; a liquid disposed in the chamber; a plurality of electrodes configured to be disposed in the chamber to define one or more spark gaps; and a pulse-generation system configured to apply voltage pulses to the plurality of electrodes at a rate of between 10 Hz and 5 MHz; where the pulse-generation system is configured to apply the voltage pulses to the plurality of electrodes such that portions of the liquid are vaporized to propagate shockwaves through the liquid and the shockwave outlet.

Some embodiments of the present apparatuses (for generating therapeutic shock waves) comprise: a housing defining a chamber and a shockwave outlet, the chamber configured to be filled with a liquid; and a plurality of electrodes disposed in the chamber to define a plurality of spark gaps; where the plurality of electrodes is configured to receive voltage pulses from a pulse-generation system at a rate of between 10 Hz and 5 MHz such that portions of the liquid are vaporized to propagate shockwaves through the liquid and the shockwave outlet.

Some embodiments of the present apparatuses (for generating therapeutic shock waves) comprise: a housing defining a chamber and a shockwave outlet, the chamber configured to be filled with a liquid; and a plurality of electrodes configured to be disposed in the chamber to define one or more spark gaps; where the plurality of electrodes is configured to receive voltage pulses from a pulse-generation system such that portions of the liquid are vaporized to propagate shockwaves through the liquid and the shockwave outlet; and where the housing comprises a translucent or transparent window that is configured to permit a user to view a region of a patient comprising target cells.

In some embodiments of the present apparatuses, the plurality of electrodes are not visible to a user viewing a region through the window and the shockwave outlet. Some embodiments further comprise: an optical shield disposed between the window and the plurality of electrodes. In some embodiments, the plurality of electrodes are offset from an optical path extending through the window and the shockwave outlet. Some embodiments further comprise: an acoustic mirror configured to reflect shockwaves from the plurality of electrodes to the shockwave outlet. In some embodiments, the acoustic mirror comprises glass. In some embodiments, the one or more spark gaps comprise a plurality of spark gaps. In some embodiments, the plurality of electrodes are configured to be removably coupled to the pulse-generation system. In some embodiments, the housing is replaceable.

Some embodiments of the present apparatuses further comprise: a spark module comprising: a sidewall configured to releasably couple the spark module to the housing; where the plurality of electrodes is coupled to the sidewall such that the plurality of electrodes is disposed in the chamber if the spark module is coupled to the housing. In some embodiments, the sidewall comprises a polymer. In some embodiments, the sidewall defines a spark chamber within which the plurality of electrodes is disposed, the spark chamber is configured to be filled with a liquid, and at least a portion of the sidewall is configured to transmit shockwaves from a liquid in the spark chamber to a liquid in the chamber of the housing. In some embodiments, the sidewall of the spark module comprises at least one of pins, grooves, or threads, and the housing comprises at least one of corresponding grooves, pins, or threads to releasably couple the spark module to the housing. In some embodiments of the present apparatuses, the housing further comprises two liquid connections. Some embodiments further comprise: a liquid reservoir; and a pump configured to circulate liquid from the reservoir to the chamber of the housing via the two liquid connectors.

In some embodiments of the present apparatuses, the pulse-generation system is configured to apply voltage pulses to the plurality of electrodes at a rate of between 20 Hz and 200 Hz. In some embodiments, the pulse-generation system is configured to apply voltage pulses to the plurality of electrodes at a rate of between 50 Hz and 200 Hz. In some embodiments, the pulse-generation system comprises: a first capacitive/inductive coil circuit comprising: an induction coil configured to be discharged to apply at least some of the voltage pulses; a switch; and a capacitor; where the capacitor and the switch are coupled in parallel between the induction coil and a current source. In some embodiments, the pulse-generation system comprises: a second capacitive/inductive coil circuit similar to the first capacitive/inductive coil circuit; and a timing unit configured to coordinate the discharge of the induction coils of each of the first and second capacitive/inductive coil circuits.

Some embodiments of the present apparatuses comprise: a spark module that comprises: a sidewall configured to releasably couple the spark module to a probe; a plurality of electrodes disposed on a first side of the sidewall and defining one or more spark gaps; and a plurality of electrical connectors in electrical communication with the plurality of electrodes and configured to releasably connect the electrodes to a pulse-generation system to generate sparks across the one or more spark gaps. In some embodiments, the sidewall comprises a polymer. In some embodiments, the sidewall defines a spark chamber within which the plurality of electrodes is disposed, the spark chamber is configured to be filled with a liquid, and at least a portion of the sidewall is configured to transmit shockwaves from a liquid in the spark chamber to a liquid in the chamber of the housing. In some embodiments, the spark module further comprises one or more liquid connectors in fluid communication with the spark chamber such that the spark chamber can be filled with a liquid. In some embodiments, the one or more liquid connectors comprise two liquid connectors through which a liquid can be circulated through the spark chamber. In some embodiments, the sidewall is configured to releasably couple the spark module to a probe having a chamber such that the electrodes are disposed within the chamber of the probe. In some embodiments, the spark module further comprises one or more liquid connectors in fluid communication with the chamber of the probe such that the chamber of the probe can be filled with a liquid through the one or more liquid connectors. In some embodiments, the one or more liquid connectors comprise two liquid connectors through which a liquid can be circulated through the chamber of the probe via the two liquid connectors.

In some embodiments of the present apparatuses comprising a spark module, the one or more spark gaps comprise a plurality of spark gaps. In some embodiments, the plurality of electrodes comprises three or four electrodes defining two spark gaps. In some embodiments, the three or four electrodes comprises a first peripheral electrode, a second peripheral electrode spaced apart from the first electrode, and one or two central electrodes configured to move back and forth between the peripheral electrodes. In some embodiments, the spark module further comprises: an elongated member coupled to the one or two central electrodes and configured to move to carry the one or two central electrodes back and forth between the peripheral electrodes. In some embodiments, the one or two central electrodes comprise two central electrodes in electrical communication with each other and disposed on opposing sides of the elongated member. In some embodiments, the elongated member is configured to self-adjust the spark gap between the peripheral electrodes and the one or two central electrodes within an expected range of operating frequencies. In some embodiments, the expected range of operating frequencies is between 10 Hz and 5 MHz. In some embodiments, the elongated member is pivotally coupled to the sidewall and biased toward an initial position by one or more spring arms. In some embodiments, the elongated member and the one or more spring arms are configured to determine a pulse rate of the spark module within an expected range of operating frequencies. In some embodiments, the expected range of operating frequencies is between 10 Hz and 5 MHz. In some embodiments, the apparatus is configured to discharge electrical pulses between the electrodes while the electrodes are submerged in a liquid such that movement of the elongated member automatically and alternatingly adjusts the spark gap between the one or two central electrodes and each of the peripheral electrodes. In some embodiments, the elongated member comprises a resilient beam having a base that is coupled in fixed relation to the sidewall. In some embodiments, the resilient beam is configured to determine a pulse rate of the spark module at expected operating conditions. In some embodiments, the apparatus is configured to discharge electrical pulses between the electrodes while the electrodes are submerged in a liquid such that movement of the resilient beam automatically and alternatingly adjusts the spark gap between the one or two central electrodes and each of the peripheral electrodes.

In some embodiments of the present apparatuses comprising a spark module, the sidewall of the spark module comprises at least one of pins, grooves, or threads, and is configured to be coupled to a probe that comprises at least one of corresponding grooves, pins, or threads to releasably couple the spark module to the housing. Some embodiments further comprise: a probe configured to be coupled to the spark module such that the plurality of electrodes is disposed in a chamber that is fillable with a liquid, and such that shockwaves originating at the electrodes will travel through a shockwave outlet of the apparatus. In some embodiments, the chamber is filled with liquid. In some embodiments, the probe does not define an additional chamber, such that the spark chamber is the only chamber through which shockwaves originating at the electrodes will propagate. In some embodiments, the probe defines a second chamber within which the spark chamber is disposed if the spark module is coupled to the probe. In some embodiments, the probe includes a plurality of electrical connectors configured to be coupled to the plurality of electrical connectors of the spark module. In some embodiments, the probe includes one or more liquid connectors configured to be coupled to the one or more liquid connectors of the spark module. In some embodiments, the probe includes two liquid connectors configured to be coupled to the two liquid connectors of the spark module. In some embodiments, the spark module is configured to be coupled to the probe such that the electrical and liquid connectors of the spark module are simultaneously connected to the respective electrical and liquid connectors of the probe as the spark module is coupled to the probe. In some embodiments, the probe includes one or more liquid connectors configured to be coupled to the one or more liquid connectors of the spark module. In some embodiments, the probe includes a combined connection having two or more electrical conductors and two lumens for communicating liquid, the combined connection configured to be coupled to a combined tether or cable that has two or more electrical conductors and two lumens for communicating liquid. In some embodiments, combined connection is configured to be removably coupled to the combined tether or cable.

In some embodiments of the present apparatuses comprising a spark module and a probe, the probe includes a housing with a translucent or transparent window that is configured to permit a user to view a region of a patient comprising target cells. In some embodiments, if the spark module is coupled to the probe, the plurality of electrodes is not visible to a user viewing a region through the window and the shockwave outlet. Some embodiments further comprise: an optical shield disposed between the window and the plurality of electrodes. In some embodiments, the optical shield includes a light-sensitive material that darkens or increases in opacity in the presence of bright light. In some embodiments, the plurality of electrodes are offset from an optical path extending through the window and the shockwave outlet. Some embodiments further comprise: an acoustic mirror configured to reflect shockwaves from the plurality of electrodes to the shockwave outlet. In some embodiments, the acoustic mirror comprises glass.

Some embodiments of the present apparatuses comprise: a probe configured to be coupled to a spark module having a plurality of electrodes defining one or more spark gaps such that the plurality of electrodes is disposed in a chamber that is finable with a liquid. In some embodiments, the chamber is filled with liquid. In some embodiments, the spark module includes a sidewall defining a spark chamber within which the plurality of electrodes are disposed, and the probe does not define an additional chamber, such that the spark chamber is the only chamber through which shockwaves originating at the electrodes will propagate. In some embodiments, the spark module includes a sidewall defining a spark chamber within which the plurality of electrodes are disposed, where the probe defines a second chamber within which the spark chamber is disposed if the spark module is coupled to the probe. In some embodiments, the probe includes a plurality of electrical connectors configured to be coupled to a plurality of electrical connectors of the spark module that are in electrical communication with the plurality of electrodes. In some embodiments, the probe includes one or more liquid connectors configured to be coupled to one or more liquid connectors of the spark module. In some embodiments, the probe includes two liquid connectors configured to be coupled to the two liquid connectors of the spark module. In some embodiments, the spark module is configured to be coupled to the probe such that the electrical and liquid connectors of the spark module are simultaneously connected to the respective electrical and liquid connectors of the probe as the spark module is coupled to the probe.

In some embodiments of the present apparatuses comprising a probe, the probe includes a combined connection having two or more electrical conductors and two lumens for communicating liquid, the combined connection configured to be coupled to a combined tether or cable that has two or more electrical conductors and two lumens for communicating liquid. In some embodiments, the combined connection is configured to be removably coupled to the combined tether or cable. In some embodiments, the probe includes a housing with a translucent or transparent window that is configured to permit a user to view a region of a patient comprising target cells. In some embodiments, if the spark module is coupled to the probe, the plurality of electrodes is not visible to a user viewing a region through the window and the shockwave outlet. Some embodiments further comprise: an optical shield disposed between the window and the plurality of electrodes. In some embodiments, the plurality of electrodes are offset from an optical path extending through the window and the shockwave outlet. Some embodiments further comprise: an acoustic mirror configured to reflect shockwaves from the plurality of electrodes to the shockwave outlet. In some embodiments, the acoustic mirror comprises glass.

Some embodiments of the present apparatuses comprising a probe further comprise: a pulse-generation system configured to repeatedly store and release an electric charge, the pulse-generation system configured to be coupled to the electrical connectors of the spark module to release the electric charge through the electrodes of the spark module. In some embodiments, the pulse-generation system is configured to apply voltage pulses to the plurality of electrodes at a rate of between 20 Hz and 200 Hz. In some embodiments, the pulse-generation system is configured to apply voltage pulses to the plurality of electrodes at a rate of between 50 Hz and 200 Hz. In some embodiments, the pulse-generation system includes a single charge/discharge circuit. In some embodiments, the pulse-generation system includes a plurality of charge/discharge circuits and a timing unit configured to coordinate charging and discharging of the plurality of charge/discharge circuits. In some embodiments, each of the charge/discharge circuits includes a capacitive/inductive coil circuit. In some embodiments, each capacitive/inductive coil circuit comprises: an induction coil configured to be discharged to apply at least some of the voltage pulses; a switch; and a capacitor; where the capacitor and the switch are coupled in parallel between the induction coil and the timing unit. Some embodiments further comprise: a liquid reservoir; and a pump configured to circulate liquid from the reservoir to the chamber of the housing.

Some embodiments of the present apparatuses comprise: a pulse-generation system including a plurality of charge/discharge circuits and a timing unit configured to coordinate charging and discharging of the plurality of charge/discharge circuits at a rate of between 10 where the pulse-generation system is configured to be coupled to a plurality of electrodes of a spark module to discharge the charge/discharge circuits through the electrodes. Some embodiments further comprise: configured each of the charge/discharge circuits includes a capacitive/inductive coil circuit. each capacitive/inductive coil circuit comprises: an induction coil configured to be discharged to apply at least some of the voltage pulses; a switch; and a capacitor; where the capacitor and the switch are coupled in parallel between the induction coil and the timing unit. the pulse-generation system is configured to apply voltage pulses to the plurality of electrodes at a rate of between 20 Hz and 200 Hz. the pulse-generation system is configured to apply voltage pulses to the plurality of electrodes at a rate of between 50 Hz and 200 Hz. Some embodiments further comprise: a liquid reservoir; and a pump configured to circulate liquid from the reservoir to the chamber of the housing.

Some embodiments of the present methods comprise: positioning the shockwave outlet of one of the present apparatuses adjacent to a region of a patient comprising target cells; and activating a pulse-generation system to propagate a shockwaves through the fluid to the target cells. In some embodiments, at least a portion of the plurality of shock waves are delivered to a portion of an epidermis layer of a patient that includes a tattoo. In some embodiments, a housing and/or probe of the apparatus includes a translucent or transparent window that is configured to permit a user to view a region of a patient comprising target cells; and the method further comprises: viewing the region through the window while positioning the apparatus. In some embodiments, the apparatus includes a spark module (that comprises: a sidewall configured to releasably couple the spark module to the housing; where the plurality of electrodes is coupled to the sidewall such that the plurality of electrodes is disposed in the chamber if the spark module is coupled to the housing), and the method further comprises: coupling the spark module to the housing prior to activating the pulse-generation system.

Some embodiments of the present methods comprise: electro-hydraulically generating a plurality of shock waves at a frequency of between 10; delivering at least a portion of the plurality of shock waves to at least one cellular structure comprising at least one region of heterogeneity; and rupturing the at least one cellular structure with the continued delivery of the plurality of shock waves. In some embodiments, the at least one region of heterogeneity comprises an effective density greater than an effective density of the at least one cellular structure. Some embodiments further comprise the step of varying the frequency of the acoustic waves. In some embodiments, at least a portion of the plurality of shock waves are delivered to an epidermis layer of a patient. In some embodiments, a portion of the epidermis layer receiving the shock waves includes cells that contain tattoo pigment particles. Some embodiments further comprise: identifying at least one target cellular structure be ruptured prior to delivering at least a portion of shock waves to the at least one target cellular structure.

Some embodiments of the present methods comprise: delivering a plurality of electro-hydraulically generated shock waves to at least one cellular structure comprising at least one region of heterogeneity until the at least one cellular structure ruptures. In some embodiments, at least a portion of the plurality of shock waves are delivered to a portion of an epidermis layer of a patient that includes cells that contain tattoo pigment particles. In some embodiments, the shock waves are delivered to the at least one cellular structure for no more than 30 minutes in a 24-hour period. In some embodiments, the shock waves are delivered to the at least one cellular structure for no more than 20 minutes in a 24-hour period. In some embodiments, between 200 and 5000 shockwaves are delivered in between 30 seconds and 20 minutes at each of a plurality of positions of a shockwave outlet. Some embodiments further comprise: tensioning a portion of a patient's skin while delivering the shockwaves. In some embodiments, the tensioning is performed by pressing a convex outlet member against the portion of the patient's skin. Some embodiments further comprise: delivering laser light to the at least one cellular structure; and/or delivering a chemical or biological agent to the at least one cellular.

Any embodiment of any of the present systems, apparatuses, and methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

Details associated with the embodiments described above and others are presented below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers. The figures are drawn to scale (unless otherwise noted), meaning the sizes of the depicted elements are accurate relative to each other for at least the embodiment depicted in the figures.

DESCRIPTION OF ILLUSTRATIVE EMBODIMENTS

Figure 1:
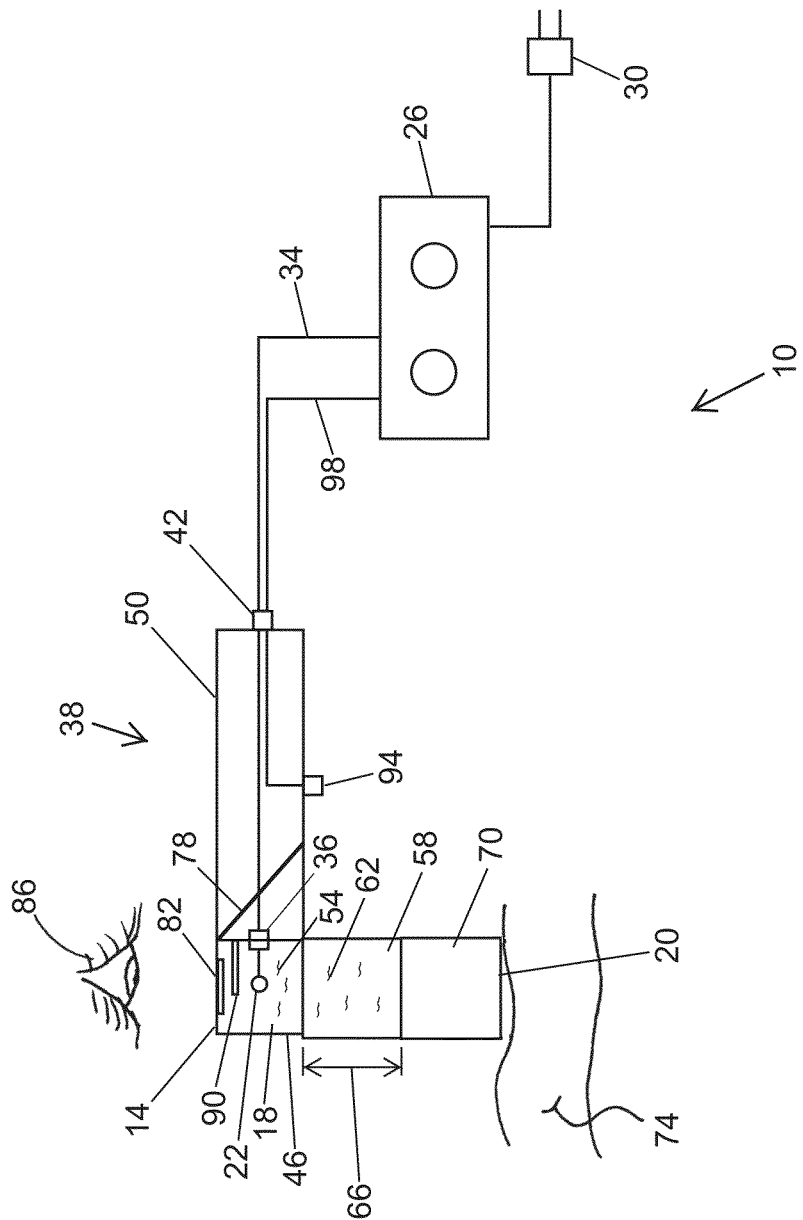
FIG. 1 depicts a block diagram of a first embodiment of the present electrohydraulic (EH) shockwave generating systems.

The term "coupled" is defined as connected, although not necessarily directly, and not necessarily mechanically; two items that are "coupled" may be unitary with each other. The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the terms "substantially," "approximately," and "about" may be substituted with "within [a percentage] of" what is specified, where the percentage includes 0.1, 1, 5, and 10 percent.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a system or apparatus that "comprises," "has," "includes" or "contains" one or more elements possesses those one or more elements, but is not limited to possessing only those elements. Likewise, a method that "comprises," "has," "includes" or "contains" one or more steps possesses those one or more steps, but is not limited to possessing only those one or more steps.

Further, a structure (e.g., a component of an apparatus) that is configured in a certain way is configured in at least that way, but it can also be configured in other ways than those specifically described.

Certain embodiments of the present systems and apparatuses are configured to generate high-frequency shock waves in a predictable and consistent manner. In some embodiments, the generated EH shock waves can be used in medical and/or aesthetic therapeutic applications (e.g., when directed at and/or delivered to target tissue of a patient). Examples of medical and/or aesthetic therapeutic applications in which the present systems can be used are disclosed in: (1) U.S. patent application Ser. No. 13/574,228, published as US 2013/0046207; and (2) U.S. patent application Ser. No. 13/547,995, published as, published as US 2013/0018287; both of which are incorporated here in their entireties. The EH shock waves generated by the present systems can be configured to impose sufficient mechanical stress to rupture in cells of the target tissue (e.g., through membrane-degradation damage).

When targeted cells (cells of target tissue) are exposed to the generated high-PR shockwaves, the cells experience sharp gradients of mechanical stress due to the spatial heterogeneity parameters of the cells, such as density and shear elasticity modulus of the different components of the cell. For instance, dense and/or inelastic components inside a cell undergo greater mechanical stress when subjected to shock waves as compared to lighter components. In particular, acceleration of higher-density particles or components within the cellular structure exposed to the impact front is typically very large. At the same time, the impact on lower-density biological structures making up the cell structure when exposed to such a large gradient of pressure is significantly reduced because the elasticity of the lower-density biological structures allows them to generally act as low-compliance material. The difference in mechanical stress results in movement of the dense and/or inelastic components within the cell.

When the cell is exposed to repeated shock waves at a certain frequency and energy level, the dense and/or inelastic components are repeatedly moved until they break out of the cell, thereby rupturing the cell. In particular, the properties mismatch of the cellular structure and cells' ability to experience deformation when exposed to the impact front lead to cellular destruction as described. One possible theory to explain the phenomenon of rupturing cellular structure can be found in (Burov, V. A., 2002) [1], which is incorporated herein by reference in its entirety.

As discussed by Burov [1], while a cell may oscillate as an integral unit when impacted by these pressure fronts, sharp gradients of mechanical stress can be generated inside the cell as a result of spatial heterogeneity parameters (i.e., density and shear elasticity modulus). This concept can be illustrated by modeling the biological structure as two linked balls with masses $m_1$ and $m_2$ and the density ($\rho_0$) of the liquid oscillating around the balls with the speed $\mu_o(t)$ differ insignificantly from the densities of the balls (by $\rho_1$ and $\rho_2$ respectively). If only the resistance to potential flow is taken into account, the force applied to the link is calculated as shown in Equation (1):

$$F = \frac{2}{3} \frac{m_1 m_2}{m_1 + m_2} \frac{[\rho_1 - \rho_2]}{\rho_0} \mu_0(t) \quad (1)$$

Additional discussions of Equation (1) and its variables are further provided in [1]. For example, if the ball radius (R) is about 10 μm and the difference between the densities of the balls is 0.1 $\rho_0$, and results in a stress force, $F/(\pi R^2)$m of $10^9$ dyne/cm², This is sufficient to rupture a cell membrane. The embodiments of the present apparatuses generate shock waves in a controlled manner that can be used to cause targeted damage to certain cells, which have medical and/or aesthetic therapeutic applications that are discussed further below.

Another possible theory to explain the phenomenon of cell rupturing is the accumulation shear stress in the denser material in the cellular structure. In heterogeneous media, such as cells with particles (e.g., pigment particles), shock waves cause the cell membranes to fail by a progressive (i.e., accumulated) shearing mechanism. On the other hand, in homogeneous media, compression by shock waves causes minimal, if any, damage to membranes. Microscopic focusing and defocusing of the shock wave as it passes through the heterogeneous media can result in shock wave strengthening or weakening locally that result in an increase in local shearing. Relative shearing motion of the cell membrane occurs on the scale of the heterogeneities of the cellular structure. It is believed that when shock waves strike a region of heterogeneities (e.g., cells containing particles), the particle motion that is out of phase with the incoming waves generates cell disruptive energy transfer (e.g., shear stress). The out of phase motion (e.g., shear stress) causes microscopic damage to the cell membrane that can progressively grow into cell membrane failure with additional successive accumulation of shear stress.

The progressive shearing mechanism of repeated exposure to shock waves can be considered dynamic fatigue of the cell membranes. Damage from dynamic fatigue is dependent on three factors: (1) applied stress or strain, (2) the rate at which the strain is applied, and (3) accumulated number of strain cycles. These three factors can be manipulated to cause a cell with heterogeneities to experience catastrophic cell membrane failure as compared to a relatively more homogeneities at a particular applied strain, strain rate, and strain cycles.

The manipulation of the factors can be done by providing EH shock waves of certain properties, such as the number of shock waves, the amount of time between each shock wave, and the strength of the applied shock waves. As discussed above, if there is too much time between shock waves for the tissue to relax to its unstrained state, the cells will become more resistant to failure. As such, in the preferred embodiment for an EH system, shock waves at a PR greater than 5 Hz and preferably greater than 100 Hz and most preferably greater than 1 MHz are delivered to the targeted cellular structures to achieve dynamic fatigue of the tissue and not allow the tissue time to relax.

At high enough PR, tissues behave as a viscous material. As a result, the PR and power level can be adjusted to account for the tissue's viscous properties.

A third possible theory is that the EH shock waves cause a combination of effects of direct movement of the particles contained in the cellular structure and dynamic fatigue that rupture the cells. While particle-containing cells are an apparent example of cellular structures exhibiting heterogeneities, their description is not intended to limit the scope of the present disclosure. Instead, the embodiments disclosed herein can be used to rupture or cause damage to other cellular structures that exhibit heterogeneities, such as cellular structures that have different effective density regions. The parameters of the shock waves generated according to the disclosed aspects can be adjusted based, at least, on the regions of different effective densities (i.e. heterogeneities) to cause cellular damage as described herein. Heterogeneities can be regions within a single cell, a region of different types of cells, or a combination of both. In certain embodiments, a region of heterogeneity within a cell includes a region having an effective density greater than the effective density of the cell. In one specific example, the effective density of a fibroblast cell is about 1.09 g/cm³, a region of heterogeneity in the cell would be particles contained within the cell that have an effective density greater than 1.09 g/cm², such as graphite with a density of 2.25 g/cm³. In certain embodiments, a region of cellular heterogeneity between cells includes a region with different types of cells, where each cell type has a different effective density, such as fibroblast cells and fat cells or hair follicles. The present disclosure provides further examples of cellular structures containing heterogeneities below.

Referring now to the drawings, and more particularly to FIG. 1, shown therein and designated by the reference numeral 10 is a block diagram of one embodiment of the present apparatuses or systems for electro-hydraulically generating shockwaves in a controlled manner. In some embodiments, such as the one shown, system 10 includes a handheld probe (e.g., with a first housing, such as in FIG. 2) and a separate controller or pulse-generation system (e.g., in or with a second housing coupled to the handheld probe via a flexible cable or the like). In other embodiments, the present systems include a single handheld apparatus disposed in a single housing.

In the embodiment shown, apparatus 10 comprises: a housing 14 defining a chamber 18 and a shockwave outlet 20; a liquid (54) disposed in chamber 18; a plurality of electrodes (e.g., in spark head or module 22) configured to be disposed in the chamber to define one or more spark gaps; and a pulse-generation system 26 configured to apply voltage pulses to the electrodes at a rate of between 10 Hz and 5 MHz. In this embodiment, the capacitive/inductive coil system 26 is configured to apply the voltage pulses to the electrodes such that portions of the liquid are vaporized to propagate shockwaves through the liquid and the shockwave outlet.

In the embodiment shown, pulse-generation system 26 is configured for use with an alternating current power source (e.g., a wall plug). For example, in this embodiment, pulse-generation system 26 comprises a plug 30 configured to be inserted into a 110V wall plug. In the embodiment shown, pulse-generation system 26 comprises a capacitive/inductive coil system, on example of which is described below with reference to FIG. 6. In other embodiment, pulse-generation system 26 can comprise any suitable structure or components configured to apply high voltages to the electrodes in a periodic fashion to generate electric sparks of sufficient power to vaporize liquid in the respective spark gaps, as described in this disclosure.

In the embodiment shown, pulse-generation system 26 is (e.g., removably) coupled to the electrodes in spark head or module 22 via a high-voltage cable 34, which may, for example, include two or more electrical conductors and/or be heavily shielded with rubber or other type of electrically insulating material to prevent shock. In some embodiments, high-voltage cable 34 is a combined tether or cable that further includes one or more (e.g., two) liquid lumens through which chamber 18 can be filled with liquid and/or via which liquid can be circulated through chamber 18 (e.g., via combined connection 36). In the embodiment shown, apparatus 10 comprises a handheld probe or handpiece 38 and cable 34 is removably coupled to probe 38 via a high-voltage connector 42, which is coupled to spark head or module 22 via two or more electrical conductors 44. In the embodiment shown, probe 38 comprises a head 46 and a handle 50, and probe 38 can comprise a polymer or other electrically insulating material to enable an operator to grasp handle 50 to position probe 38 during operation. For example, handle 50 can be molded with plastic and/or can be coated with an electrically insulating material such as rubber.

In the embodiment shown, a liquid 54 (e.g., a dielectric liquid such as distilled water) is disposed in (e.g., and substantially fills) chamber 18. In this embodiment, spark head 22 is positioned in chamber 18 and surrounded by the liquid such that the electrodes can receive voltage pulses from pulse-generation system 26 (e.g., at a rate of between 10 Hz and 5 MHz) such that portions of the liquid are vaporized to propagate shockwaves through the liquid and shockwave outlet 20. In the embodiment shown, probe 38 includes an acoustic delay chamber 58 between chamber 18 and outlet 20. In this embodiment, acoustic delay chamber is substantially filled with a liquid 62 (e.g., of the same type as liquid 54) and has a length 66 that is sufficient to permit shockwaves to form and/or be directed toward outlet 20. In some embodiments, length 66 may be between 2 millimeters (mm) and 25 millimeters (mm). In the embodiment shown, chamber 18 and acoustic-delay chamber 58 are separated by a layer of sonolucent (acoustically permeable or transmissive) material that permits sound waves and/or shockwaves to travel from chamber 18 into acoustic-delay chamber 58. In other embodiments, liquid 62 may be different than liquid 54 (e.g., liquid 62 may comprise bubbles, water, oil, mineral oil, and/or the like). Certain features such as bubbles may introduce and/or improve a nonlinearity in the acoustic behavior of liquid 54 to increase the formation of shockwaves. In further embodiments, chamber 18 and acoustic-delay chamber 54 may be unitary (i.e., may comprise a single chamber). In further embodiments, acoustic-delay chamber 54 may be replaced with a solid member (e.g., a solid cylinder of elastomeric material such as polyurethane). In the embodiment shown, probe 38 further includes an outlet member 70 removably coupled to the housing at a distal end of the acoustic delay chamber, as shown. Member 70 is configured to contact tissue 74, and can be removed and either sterilized or replaced between patients. Member 70 comprises a polymer or other material (e.g., low-density polyethylene or silicone rubber) that is acoustically permeable to permit shockwaves to exit acoustic-delay chamber 58 via outlet 20. Tissue 74 may, for example, be human skin tissue to be treated with apparatus 10, and may, for example, include a tattoo, a blemish, a subdermal lesion, or a basal cell abnormality. In some embodiments, an acoustic coupling gel (not shown) may be disposed between member 70 and tissue 74 to lubricate and provide additional acoustic transmission into tissue 74.

In the embodiment shown, probe 38 includes an acoustic mirror 78 that comprises a material (e.g., glass) and is configured to reflect a majority of sound waves and/or shock waves that are incident on the acoustic mirror. As shown, acoustic mirror 58 can be angled to reflect sound waves and/or shockwaves (e.g., that originate at spark head 22) toward outlet 20 (via acoustic-delay chamber). In the embodiment shown, housing 14 can comprise a translucent or transparent window 82 that is configured to permit a user to view (through window 82, chamber 18, chamber 58, and member 70) a region of a patient (e.g., tissue 74) comprising target cells (e.g., during application of shockwaves or prior to application of shockwaves to position outlet 20 at the target tissue). In the embodiment shown, window 82 comprises an acoustically reflective material (e.g., glass) that is configured to reflect a majority of sound waves and/or shock waves that are incident on the window. For example, window 82 can comprise clear glass of sufficient thickness and strength to withstand the high-energy acoustic pulses produced at spark head 22 (e.g., tempered plate glass having a thickness of about 2 mm and an optical transmission efficiency of greater than 50%).

In FIG. 1, a human eye 86 indicates a user viewing the target tissue through window 82, but it should be understood that target tissue may be "viewed" through window 82 via a camera (e.g., a digital still and/or video camera). By direct or indirect observation, acoustic energy can be positioned, applied, and repositioned according to target tissues, such as extant tattoos, and by indications of acoustic energy, such as a change in the color of the tissue. However, if spark head 22 is disposed where a user can view spark head 22, the brightness of the resulting spark from spark head 22 may be too bright for a user to comfortably view, and in the embodiment shown, probe 38 is configured such that the plurality of electrodes are not visible to a user viewing a region (e.g., of target tissue) through window 82 and outlet 20. For example, in the embodiment shown, probe 38 includes an optical shield 90 disposed between spark head 22 and window 82. Shield 90, for example, can have a width and/or a length that are less than a corresponding width and/or length of window 82 such that shield 90 is large enough to substantially block light from spark head 22 from traveling directly to the user's eye, but does not interfere with the field-of-view through window 82 and outlet 20 more than is necessary to block that light. Shield 90 can, for example, comprise a thin sheet of metal, such as stainless steel, or other opaque material, or can comprise welder's glass (e.g., an LCD darkened by a photocell or other light-sensitive material) that is optically activated and darkened by the brightness of sparks at the spark gaps. The acoustic effect of shielding the resulting sparks from a spark gap head must be considered in order to maintain the effect of a point source from spark head 22 and a resulting desired planar wavefront. If shield 90 comprises an acoustically reflective material, to prevent pulse broadening, the distance between the shield and the spark gaps between electrodes in spark head 22 may be selected to minimize (e.g., at least destructive) interference between sound waves and/or shockwaves reflected from the shield and sound waves and/or shockwaves originating at spark head 22 (e.g., such that intersecting waves do not produce excess echoes or reverberation). With a velocity of sound waves in a medium such as distilled water of about 1500 m/Sec, the distance between the spark head and the shield may be calculated to be at ½ and ¾ wavelengths from the source.

Spark head 22 (e.g., the electrodes in spark head 22) may have a limited lifetime that may be extended by limiting the duration of activation. In the embodiment shown, apparatus 10 includes a switch or trigger 94 coupled to pulse-generation system 26 via a switch wire or other connection 98 through connector 42, such that switch 94 can be actuated to apply voltage pulses to the electrodes in spark head 22.

Figure 2:
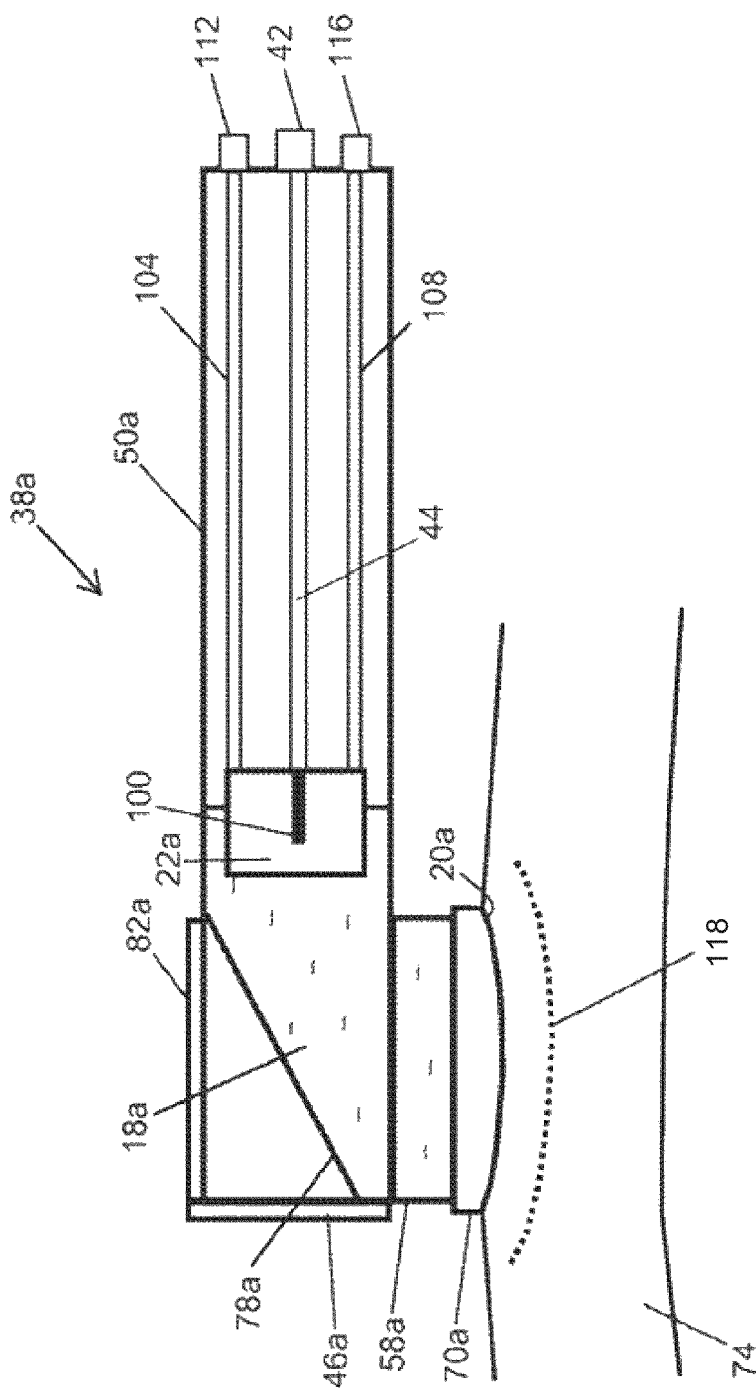
FIG. 2 depicts a cross-sectional side view of a handheld probe for some embodiments of the present EH shockwave generating systems.

FIG. 2 depicts a cross-sectional side view of a second embodiment 38a of the present handheld probes or handpiece for use with some embodiments of the present EH shockwave generating systems and apparatuses. Probe 38a is substantially similar in some respects to probe 38, and the differences are therefore primarily described here. For example, probe 38a is also configured such that the plurality of electrodes of spark head or module 22a are not visible to a user viewing a region (e.g., of target tissue) through window 82a and outlet 20a. However, rather than including an optical shield, probe 38a is configured such that spark head 22a (and the electrodes of the spark head) are offset from an optical path extending through window 82a and outlet 20a. In this embodiment, acoustic mirror 78a is positioned between spark head 22a and outlet 20a, as shown, to define a boundary of chamber 18a and to direct acoustic waves and/or shockwaves from spark head 22a to outlet 20a. In the embodiment shown, window 82a can comprise a polymer or other acoustically permeable or transmissive material because acoustic mirror 78a is disposed between window 82a and chamber 18a and sound waves and/or shockwaves are not directly incident on window 82a (i.e., because the sound waves and/or shock waves are primarily reflected by acoustic mirror 78a).

In the embodiment shown, spark head 22a includes a plurality of electrodes 100 that define a plurality of spark gaps. The use of multiple spark gaps can be advantageous because it can double the number of pulses that can be delivered in a given period of time. For example, after a pulse vaporizes an amount of liquid in a spark gap the vapor must either return to its liquid state or must be displaced by a different portion of the liquid that is still in a liquid state. In addition to the time required for the spark gap to be re-filled with water before a subsequent pulse can vaporize additional liquid, sparks also heat the electrodes. As such, for a given spark rate, increasing the number of spark gaps reduces the rate at which each spark gap must be fired and thereby extends the life of the electrodes. Thus, ten spark gaps potentially increases the possible pulse rate and/or electrode life by a factor of ten.

As noted above, high pulse rates can generate large amounts of heat that may increase fatigue on the electrodes and/or increase the time necessary for vapor to return to the liquid state after it is vaporized. In some embodiments, this heat can be managed by circulating liquid around the spark head. For example, in the embodiment of FIG. 2, probe 38 includes conduits 104 and 108 extending from chamber 18a to respective connectors 112 and 116, as shown. In this embodiment, connectors 112 and 116 can be coupled to a pump to circulate liquid through chamber 18a (e.g., and through a heat exchanger. For example, in some embodiments, pulse-generation system 26 (FIG. 1) can comprise a pump and a heat exchanger in series and configured to be coupled to connectors 112 and 116 via conduits or the like. In some embodiments, a filter can be included in probe 38a, in a spark generation system (e.g., 26), and/or between the probe and the spark generation system to filter liquid that is circulated through the chamber Additionally, due to the limited life of electrodes 100 at high pulse rates, some embodiments of the present probes may be disposable. Alternatively, some embodiments are configured to permit a user to replace the electrodes. For example, in the embodiment of FIG. 2, spark head 22a is configured to be removable from probe 38a. For example, spark head 22a may be removable through handle 50a, or handle 50a may be removably coupled (e.g., via threads or the like) to head 46a such that upon removal of handle 50a from head 46, spark head 22a can be removed from head 46a and replaced.

As illustrated in FIG. 2, application of each shockwave to a target tissue includes a wavefront 118 propagating from outlet 20a and traveling outward through tissue 74. As shown, wavefront 74 is curved according to its expansion as it moves outwardly and partially according to the shape of the outer surface of outlet member 70a that contacts tissue 74. In other embodiments, such as that of FIG. 1, the outer shape of the contact member can be planar or otherwise shaped to affect certain properties of the wavefront as it passes through outlet 20a and propagates through the target tissue.

Figure 2A:
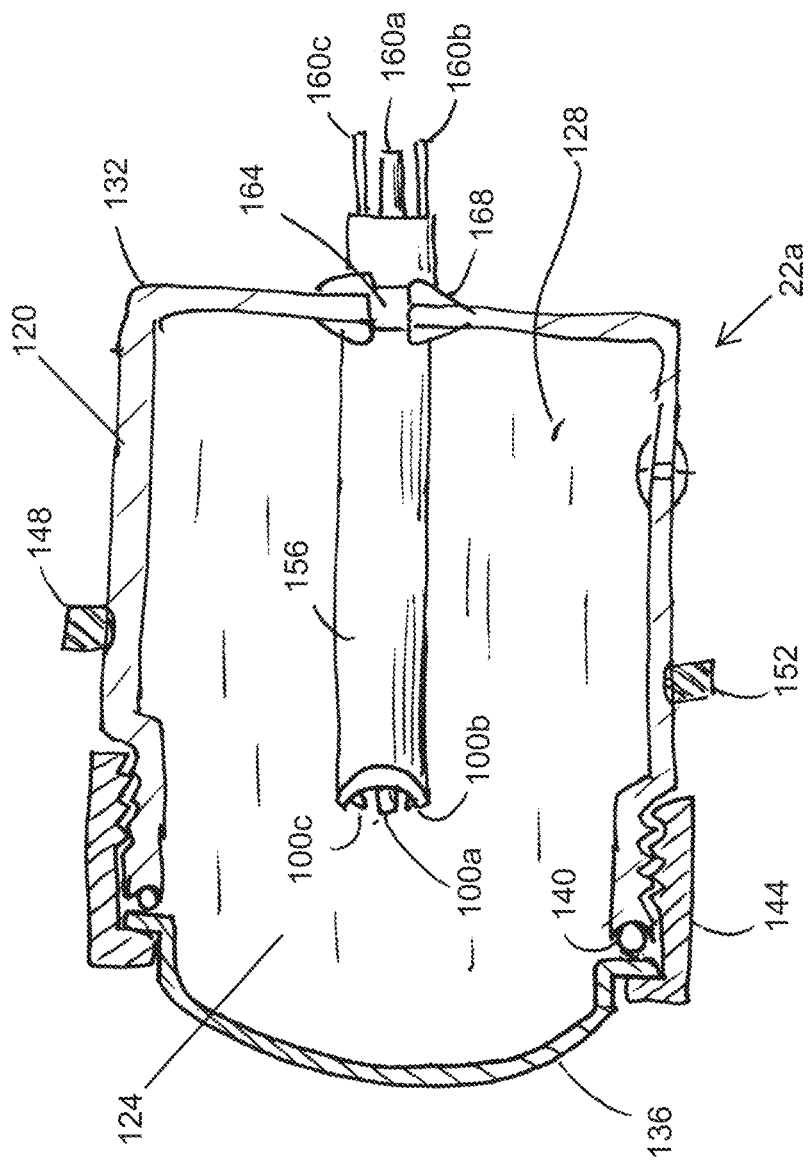
FIG. 2A depicts a cross-sectional side view of a first embodiment of a removable spark head usable with embodiments of the present handheld probes, such as the one of FIG. 2.

FIG. 2A depicts an enlarged cross-sectional view of first embodiment of a removable spark head or module 22a. In the embodiment shown, spark head 22a comprises a sidewall 120 defining a spark chamber 124, and a plurality of electrodes 100a, 100b, 100c disposed in the spark chamber. In the embodiment shown, spark chamber 124 is filled with liquid 128 which may be similar to liquid 54 (FIG. 1). At least a portion of sidewall 120 comprises an acoustically permeable or transmissive material (e.g., a polymer such as polyethylene) configured to permit sound waves and/or shockwaves generated at the electrodes to travel through sidewall 120 and through chamber 18a. For example, in the embodiment shown, spark head 22a includes a cup-shaped member 132 that may be configured to be acoustically reflective and an acoustically permeable cap member 136. In this embodiment, cap member 136 is dome shaped to approximate the curved shape of an expanding wavefront that originates at the electrodes and to compress the skin when applied with moderate pressure. Cap member 136 can be coupled to cup-shaped member 132 with an O-ring or gasket 140 and a retaining collar 144. In the embodiment shown, cup-shaped member 132 has a cylindrical shape with a circular cross-section (e.g., with a diameter of 2 inches or less). In this embodiment, cup-shaped member includes bayonet-style pins 148, 152 configured to align with corresponding grooves in head 46a of probe 38a (FIG. 2) to lock the position of spark head 22a relative to the probe.

In the embodiment shown, an electrode core 156 having conductors 160a, 160b, 160c and extending through aperture 164, with the interface between aperture 164 and electrode core 156 sealed with a grommet 168. In the embodiment shown, a central conductor 160a extends through the center of core 156 and serves as a ground to corresponding center electrode 100a. Peripheral conductors 160b, 160c are in communication with peripheral electrodes 100b, 100c to generate sparks across the spark gap between electrodes 100a and 100b, and between electrodes 100a and 100c. It should be understood that while two spark gaps are shown, any number of spark gaps may be used, and may be limited only by the spacing and size of the spark gaps. For example, other embodiments include 3, 4, 5, 6, 7, 8, 9, 10, or even more spark gaps.

Figure 2B:
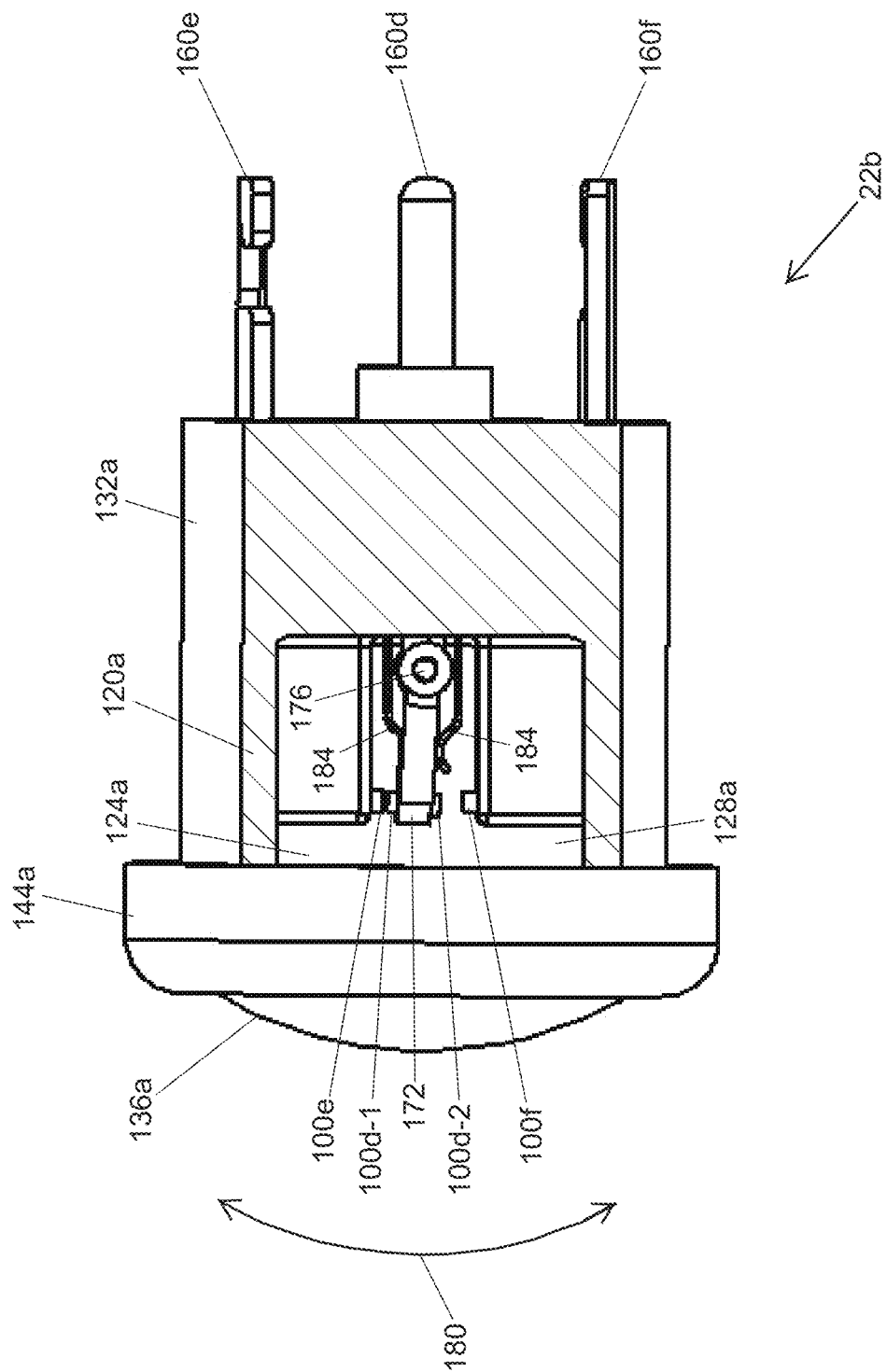
FIG. 2B depicts a cutaway side view of a second embodiment of a removable spark usable with embodiments of the present handheld probes, such as the one of FIG. 2.

FIG. 2B depicts an enlarged cutaway side view of a second embodiment of a removable spark head or module 22b. In the embodiment shown, spark head or module 22b comprises a sidewall 120a defining a spark chamber 124a, and a plurality of electrodes 100d-1, 100d-2, 100, 100f disposed in the spark chamber. In the embodiment shown, spark chamber 124a is filled with liquid 128a which may be similar to liquid 128 and/or 54. At least a portion of sidewall 120a comprises an acoustically permeable or transmissive material (e.g., a polymer such as polyethylene) configured to permit sound waves and/or shockwaves generated at the electrodes to travel through sidewall 120a and through chamber 18a (FIG. 2). For example, in the embodiment shown, spark head 22b includes a cup-shaped member 132a that may be configured to be acoustically reflective and an acoustically permeable cap member 136a. In this embodiment, cap member 136a is dome shaped to approximate the curved shape of an expanding wavefront that originates at the electrodes and to compress the skin when applied with moderate pressure. Cap member 136a can be coupled to cup-shaped member 132a with an O-ring or gasket (not shown, but similar to 140) and a retaining collar 144a. In the embodiment shown, cup-shaped member 132a has a cylindrical shape with a circular cross-section (e.g., with a diameter of 2 inches or less. In some embodiments, cup-shaped member can also include bayonet-style pins (not shown, but similar to 148, 152) configured to align with corresponding grooves in head 46a of probe 38a to lock the position of spark head 22b relative to the probe.

In the embodiment shown, conductors 160 *d*, 160 *e*, 160 *f* extending through a rear portion (opposite outlet cap member 136 *a*) of cup-shaped member 132 *a*, as shown. In this embodiment, central conductor 160 *d* and peripheral conductors 160 *e*, 160 *f* can be molded into sidewall 120 *a* such that grommets and the like are not necessary to seal the interface between the sidewall and the conductors. In the embodiment shown, a central conductor 160 *d* serves as a ground to corresponding center electrodes 100 *d*–1 and 100 *d*–2, which are also in electrical communication with each other. Peripheral conductors 160 *e*, 160 *f* are in communication with peripheral electrodes 100 *e*, 100 *f* to generate sparks across the spark gap between electrodes 100 *d*–1 and 100 *e*, and between electrodes 100 *d*–2 and 100 *f*. It should be understood that while two spark gaps are shown, any number of spark gaps may be used, and may be limited only by the spacing and size of the spark gaps. For example, other embodiments include 3, 4, 5, 6, 7, 8, 9, 10, or even more spark gaps.

In the embodiment shown, central electrodes 100*d*–1 and 100*d*–2 are carried by, and may be unitary with, an elongated member 172 extending into chamber 124a toward cap member 136a from sidewall 120a. In this embodiment, member 172 is mounted to a hinge 176 (which is fixed relative to sidewall 120a) to permit the distal end of the member (adjacent electrodes 100*d*–1, 100*d*–2 to pivot back and forth between electrodes 100*e* and 100*f*, as indicated by arrows 180. In the embodiment shown, the distal portion of member 172 is biased toward electrode 100*e* by spring arms 184. In this embodiment, spring arms 184 are configured to position electrode 100*d*–1 at an initial spark gap distance from electrode 100*e*. Upon application of an electrical potential (e.g., via a pulse-generation system, as described elsewhere in this disclosure) across electrodes 100*d*–1 and 100*e*, a spark will arc between these two electrodes to release an electric pulse to vaporize liquid between these two electrodes. The expansion of vapor between these two electrodes drives member 172 and electrode 100*d*–2 downward toward electrode 100*f*. During the period of time in which member 172 travels downward, the pulse-generation system can re-charge and apply an electric potential between electrodes 100*d*–2 and 100*f*, such that when the distance between electrodes 100*d*–2 and 100*f* becomes small enough, a spark will arc between these two electrodes to release the electric pulse to vaporize liquid between these two electrodes. The expansion of vapor between electrodes 100*d*–2 and 100*f* then drives member 172 and electrode 100*d*–1 upward toward electrode 100*e*. During the period of time in which member 172 travels upward, the pulse-generation system can re-charge and apply an electric potential between electrodes 100*d*–1 and 100*e*, such that when the distance between electrodes 100*d*–1 and 100*e* becomes small enough, a spark will arc between these two electrodes to release the electric pulse and vaporize liquid between these two electrodes, causing the cycle to begin again. In this way, member 172 oscillates between electrodes 100*e* and 100*f* until the electric potential ceases to be applied to the electrodes.

The exposure to high-rate and high-energy electric pulses, especially in liquid, subjects the electrodes to rapid oxidation, erosion, and/or other deterioration that can vary the spark gap distance between electrodes if the electrodes are held in fixed positions (e.g., requiring electrodes to be replaced and/or adjusted). However, in the embodiment of FIG. 2B, the pivoting of member 172 and electrodes 100*d*–1, 100*d*–2 between electrodes 100*e* and 100*f* effectively adjusts the spark gap for each spark. In particular, the distance between electrodes at which current arcs between the electrodes is a function of electrode material and electric potential. As such, once the nearest surfaces (even if eroded) of adjacent electrodes (e.g., 100*d*–1 and 100*e*) reach a spark gap distance for a given embodiment, a spark is generated between the electrodes. As such, member 172 is configured to self-adjust the respective spark gaps between electrodes 100*d*–1 and 100*e*, and between electrodes 100*d*–2 and 100*f*.

Another example of an advantage of the present movable electrodes, as in FIG. 2B, is that multiple coils are not required as long as the electrodes are positioned such that only one pair of electrodes is within arcing distance at any given time, and such a single coil or coil system is configured to recharge in less time than it takes for member 172 to pivot from one electrode to the next. For example, in the embodiment of FIG. 2B, an electric potential may simultaneously be applied to electrodes 100*e* and 100*f* with electrodes 100*d*–1 and 100*d*–2 serving as a common ground, with the electric potential such that a spark will only arc between electrodes 100*d*–1 and 100*e* when member 172 is pivoted upward relative to horizontal (in the orientation shown), and will only arc between electrodes 100*d*–2 and 100*f* when member 172 is pivoted downward relative to horizontal. As such, as member 172 pivots upward and downward as described above, a single coil or coil system can be connected to both of peripheral electrodes 100*e*, 100*f* and alternately discharged through each of the peripheral electrodes. In such embodiments, the pulse rate can be adjusted by selecting the physical properties of member 172 and spring arms 184. For example, the properties (e.g., mass, stiffness, cross-sectional shape and area, length, and/or the like) of member 172 and the properties (e.g., spring constant, shape, length, and/or the like) of spring arms 184 can be varied to adjust a resonant frequency of the system, and thereby the pulse rate of the spark head or module 22b. Similarly, the viscosity of liquid 128a may be selected or adjusted (e.g., increased to reduce the speed of travel of arm 172, or decreased to increase the speed of travel of arm 172).

Another example of an advantage of the present movable electrodes, as in FIG. 2B, is that properties (e.g., shape, cross-sectional area, depth, and the like) of the electrodes can be configured to achieve a known effective or useful life for the spark head (e.g., one 30-minute treatment) such that spark head 22b is inoperative or of limited effectiveness after that designated useful life. Such a feature can be useful to ensure that the spark head is disposed of after a single treatment, such as, for example, to ensure that a new, sterile spark head is used for each patient or area treated to minimize potential cross-contamination between patients or areas treated.

Figure 2C:
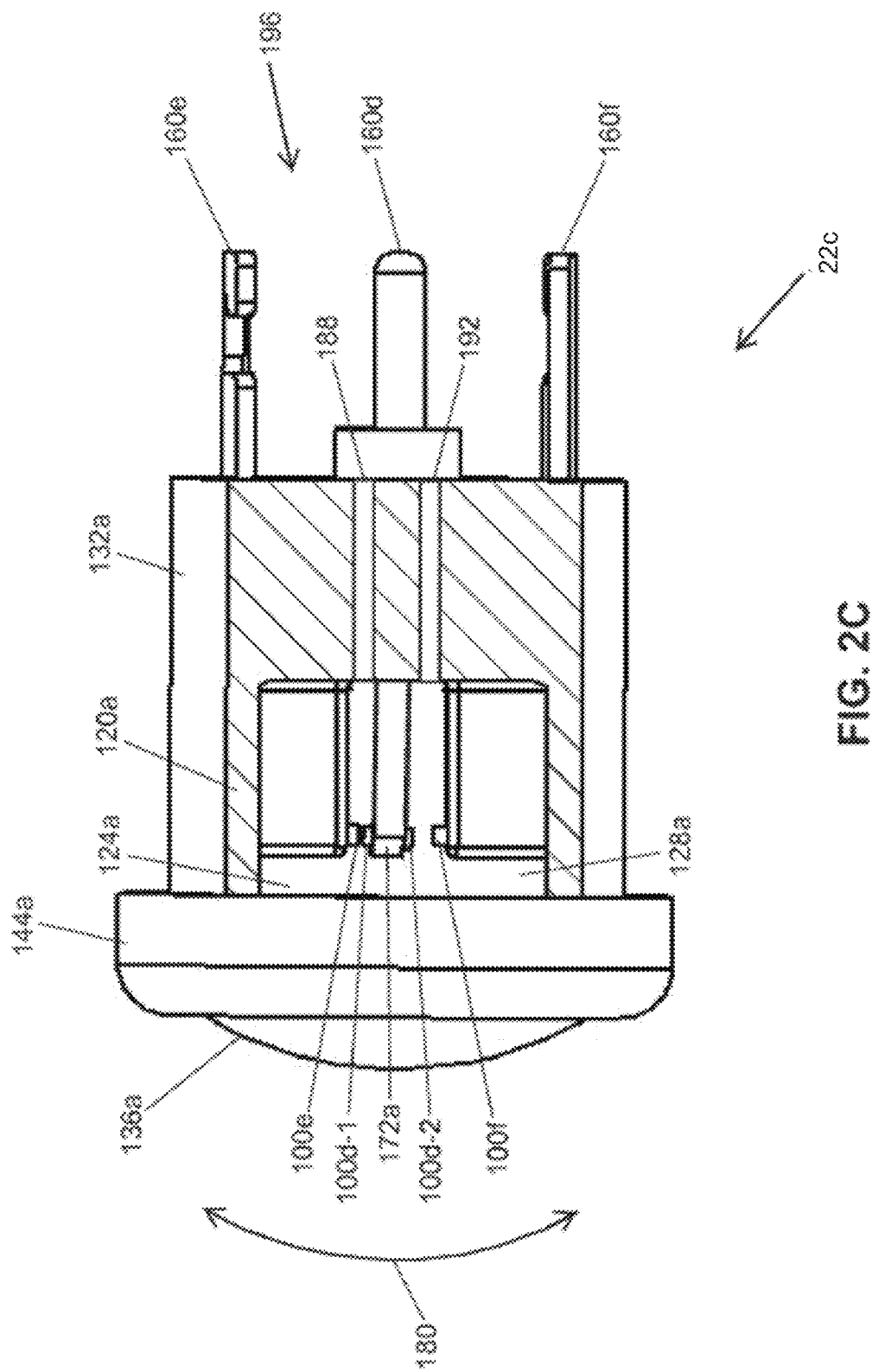
FIG. 2C depicts a cutaway side view of a third embodiment of a removable spark head usable with embodiments of the present handheld probes, such as the one of FIG. 2.

FIG. 2C depicts an enlarged cutaway side view of a third embodiment of a removable spark head or module 22c.

Spark head 22c is substantially similar to spark head 22b, except as noted below, and similar reference numerals are therefore used to designate structures of spark head 22c that are similar to corresponding structures of spark head 22b. The primary difference relative to spark head 22b is that spark head 22c includes a beam 172a that does not have a hinge, such that flexing of the beam itself provides the movement of electrodes 100d-1 and 100d-2 in the up and down directions indicated by arrows 180, as described above for spark head 22b. In this embodiment, the resonant frequency of spark head 22c is especially dependent on the physical properties (e.g., mass, stiffness, cross-sectional shape and area, length, and/or the like) of beam 172a. As described for spring arms 184 of spark head 22b, beam 172a is configured to be biased toward electrode 100e, as shown, such that electrode 100d-1 is initially positioned at an initial spark gap distance from electrode 100e. The function of spark head 22c is similar to the function of spark head 22b, with the exception that beam 172a itself bends and provides some resistance to movement such that hinge 176 and spring arms 184 are unnecessary.

In the embodiment shown, spark head 22b also includes liquid connectors or ports 188, 192 via which liquid can be circulated through spark chamber 124b. In the embodiment shown, a proximal end 196 of spark head 22b serves as a combined connection with two lumens for liquid (connectors or ports 188, 192) and two or more (e.g., three, as shown) electrical conductors (connectors 160d, 160e, 160f). In such embodiments, the combined connection of proximal end 196 can be coupled (directly or via a probe or handpiece) to a combined tether or cable having two liquid lumens (corresponding to connectors or ports 188, 192), and two or more electrical conductors (e.g., a first electrical conductor for connecting to connector 160d and a second electrical conductor for connecting to both peripheral connectors 160e, 160f). Such a combined tether or cable can couple the spark head (e.g., and a probe or handpiece to which the spark head is coupled) to a pulse-generation system having a liquid reservoir and pump such that the pump can circulate liquid between the reservoir and the spark chamber. In some embodiments, cap member 136a is omitted such that connectors or ports 188, 192 can permit liquid to be circulated through a larger chamber (e.g., 18a) of a handpiece to which the spark head is coupled. Likewise, a probe or handpiece to which spark head 22a is configured to be coupled can include electrical and liquid connectors corresponding to the respective electrical connectors (160d, 160e, 160f) and liquid connectors (188, 192) of the spark head such that the electrical and liquid connectors of the spark head are simultaneously connected to the respective electrical and liquid connectors of the probe or handpiece as the spark module is coupled to the handpiece (e.g., via pressing the spark head and probe together and/or a twisting or rotating the spark head relative probe).

In the present embodiments, a pulse rate of a few Hz to many KHz (e.g., up to 5 MHz) may be employed. Because the fatiguing event produced by a plurality of pulses, or shockwaves, is generally cumulative at higher pulse rates, treatment time may be significantly reduced by using many moderately-powered shockwaves in rapid succession rather than a few higher powered shockwaves spaced by long durations of rest. As noted above, at least some of the present embodiments (e.g., those with multiple spark gaps) enable electrohydraulic generation of shockwaves at higher rates. For example, FIG. 3A depicts a timing diagram enlarged to show only two sequences of voltage pulses applied to the electrodes of the present embodiments, and FIG. 3B depicts a timing diagram showing a greater number of voltage pulses applied to the electrodes of the present embodiments.

In additional embodiments that are similar to any of spark modules 22 a, 22 b, 22 c, a portion of the respective sidewall (120, 120 a) may be omitted such that the respective spark chamber (124, 124 a, 124 b) is also omitted or left open such that liquid in a larger chamber (e.g., 18 or 18 a) of a corresponding handpiece can freely circulate between the electrodes. In such embodiments, the spark chamber (e.g., sidewall 120, 120 a) can include liquid connectors or liquid may circulate through liquid ports that are independent of spark chamber (e.g., as depicted in FIG. 2).

Figures 3A, 3B:
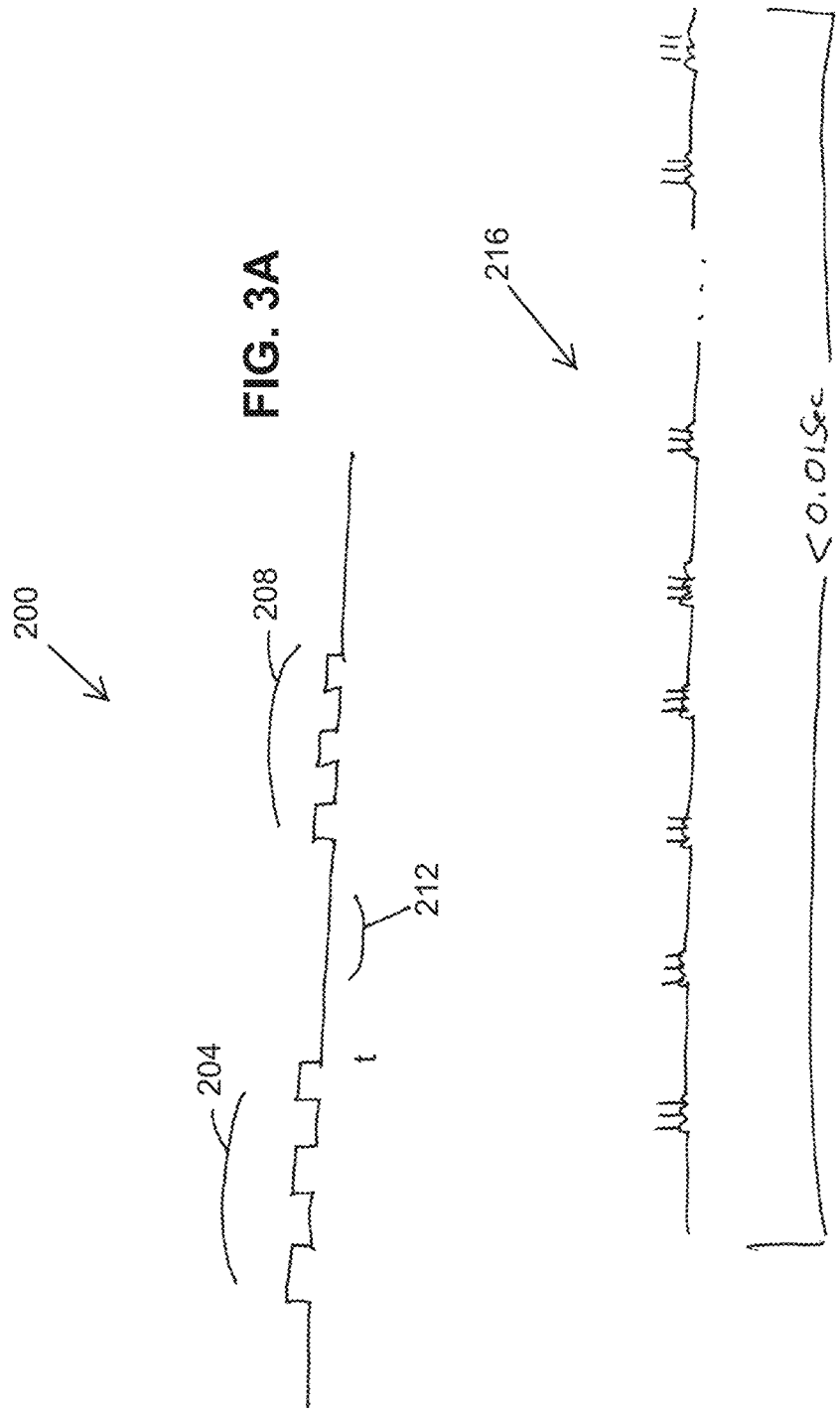
FIG. 3A-3B depict a timing diagrams of one example of the timed application of energy cycles or voltage pulses in the system of FIG. 1 and/or the handheld probe of FIG. 2.

The portion of pulse train or sequence 200 shown in FIG. 3A includes pulse groups 204 and 208 timed with a delay period 212 in between. Bursts or groups (e.g., 204, 208) may include as few as one or two, or as many as thousands, of pulses. In general, each group 204, 208 can include several voltage pulses that are applied to the electrodes to trigger an event (i.e., a spark across a spark gap). The duration of delay period 212 can be set to allow cooling of the electrodes across each spark gap and to allow recharging of the electronics. As used for the embodiments of this disclosure, pulse rate refers to the rate at which voltage pulse groups (each having one or more pulses) are applied to the electrodes; meaning that individual pulses within pulse groups having two or more pulses are applied at a greater frequency, as illustrated in FIGS. 3A-3B. Each of these pulse groups can be configured to generate one shock wave or a plurality of shock waves.

A series of events (sparks) initiated by a plurality of bursts or groups 204 and 208 delivered with the present systems and apparatuses can comprise a higher pulse rate (PR) that can reduce treatment time relative to lower PRs which may need to be applied over many minutes. Tattoos, for example, may encompass broad areas and therefore are time consuming to treat unless rapid cell destruction is achieved (e.g., with the higher PRs of the present disclosure). In contrast to the prior art systems noted above, the present embodiments can be configured to deliver shock waves at a relatively high PR 216 of 10 to 5000 or more pulses per second (e.g., greater than any one of, or between any two of: 10 Hz, 30 Hz, 50 Hz, 1000 Hz, 10000 Hz, 1000000 Hz, 500000 Hz, and/or 5000000.

Figure 4:
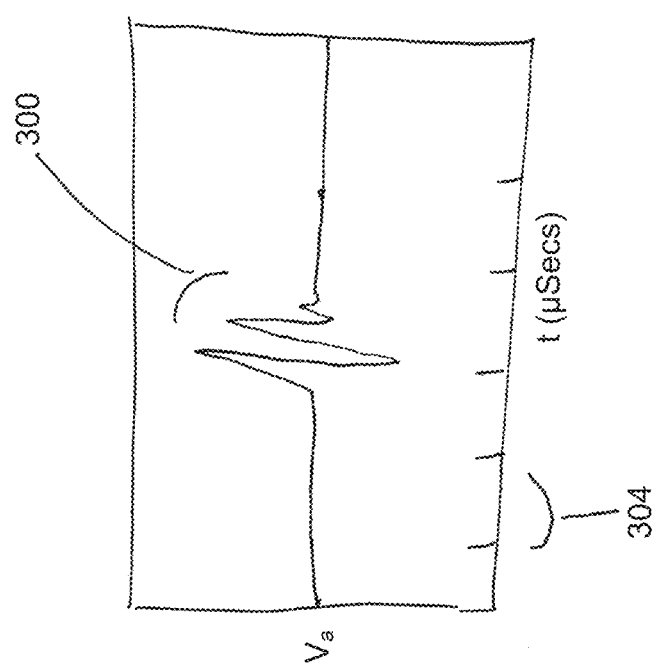
FIG. 4 depicts a waveform that can be emitted by system of FIG. 1 and/or the handheld probe of FIG. 2 into target tissue.

FIG. 4 depicts a waveform that can emitted by either of probes 38 or 38a into a volume of tissue, and that is of a form that can be useful for the elimination of tattoos. Pulse 300 is of a typical shaped for an impulse generated by the present EH spark heads at relatively high-voltage pulses. For example, pulse 300 has a rapid rise time, a short duration, and a ring down period. The units of vertical axis $V_a$ are arbitrary as may be displayed on an oscilloscope. The actual acoustic pulse amplitude may be as low as 50 μPa and as high as several MPa in various ones of the present embodiments, at least because cumulative energy delivery may be effective, as discussed above. The individual time periods 304 may be 100 nano-seconds each, which corresponds to short pulse lengths referred to in the art as "shockwave" pulses, owing to their sharpness and short rise and fall times. For example, a rise time of <30 nanoseconds is considered to be a shockwave for purposes of the present disclosure, the rapidity being particularly effective for producing relative large pressure-temporal pressure gradients across small, cellular-scaled structures in tissue (e.g., the dermis). Rapid compression and decompression of dermal structures containing tattoo "inks" which are actually particulate pigments, results in a fatiguing and destruction of the pigment-containing cells over time and is believed to be one underlying mechanism of the present methods, as described above. For example, agitation of tissue with such shock waves has been shown to be effective, when applied at high pulse rates within a relatively short time period, and at sufficient energy levels to produce a pigmented cell to rupture, with resulting liberation of entrapped particulates and subsequent dissemination of the pigment particles into the body, thereby reducing the appearance of the tattoo. It is believed to be necessary to have a short pulse waveform 300, which may be applied multiple times and preferably many hundreds to millions of times to an area to be treated to produce the fatigue needed for tattoo "ink" removal.

Figure 5:
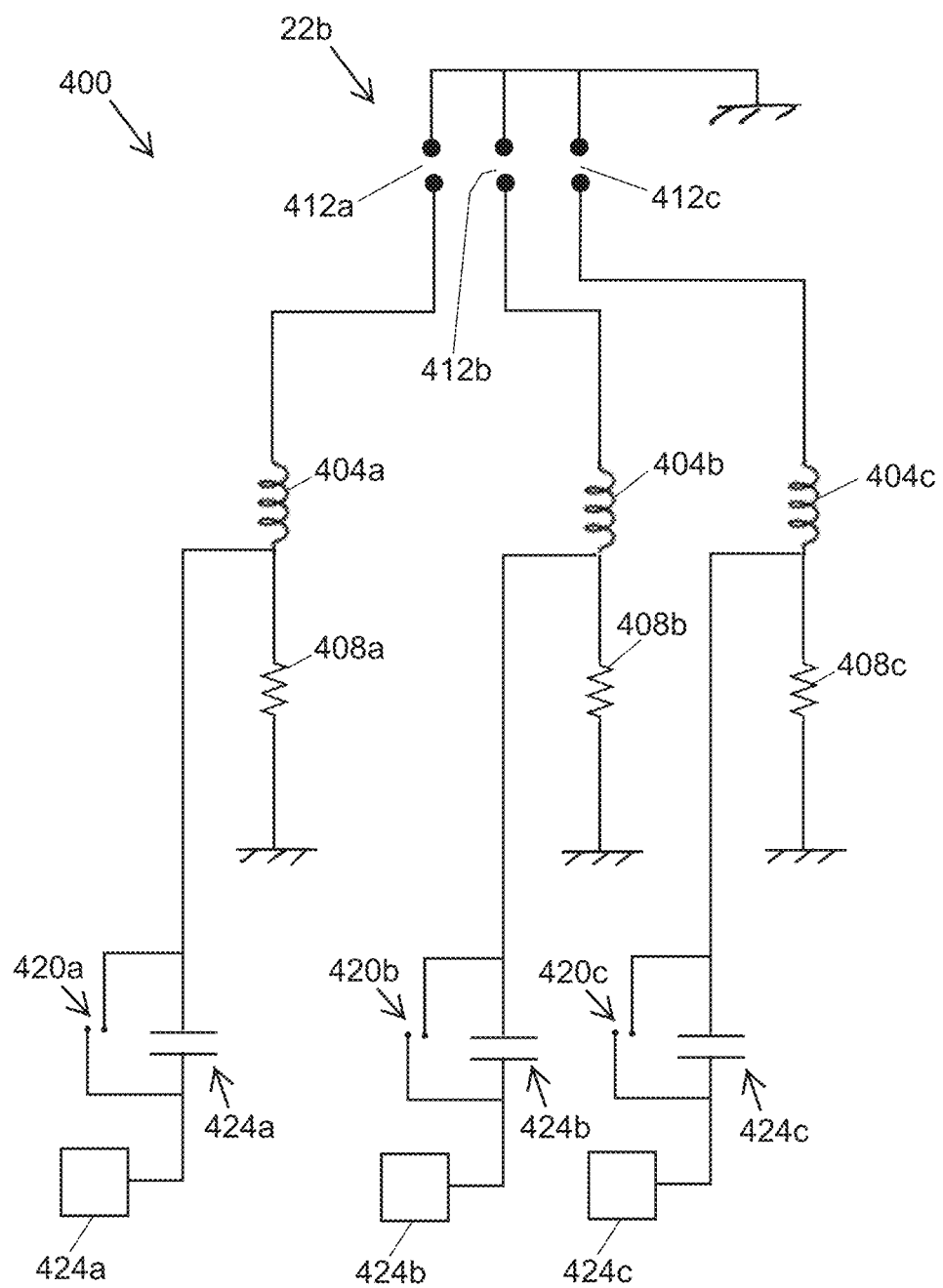
FIG. 5 depicts a schematic diagram of one embodiment of a multi-gap pulse-generation system for use in or with some embodiments of the present systems.

FIG. 5 depicts a schematic diagram of one embodiment 400 of a pulse-generation system for use in or with some embodiments of the present systems. In the embodiment shown, circuit 400 comprises a plurality of charge storage/discharge circuits each with a magnetic storage or induction type coil 404a, 404b, 404c (e.g., similar to those used in automotive ignition systems). As illustrated, each of coils 404a, 404b, 404c, may be grounded via a resistor 408a, 408b, 408c to limit the current permitted to flow through each coil, similar to certain aspects of automotive ignition systems. Resistors 408a, 408b, 408c can each comprise dedicated resistors, or the length and properties of the coil itself may be selected to provide a desired level of resistance. The use of components of the type used automotive ignition systems may reduce costs and improve safety relative to custom components. In the embodiment shown, circuit 400 includes a spark head 22b that is similar to spark head 22a with the exceptions that spark head 22b includes three spark gaps 412a, 412b, 412c instead of two, and that each of the three spark gaps is defined by a separate pair of electrodes rather than a common electrode (e.g., 100a) cooperating with multiple peripheral electrodes. It should be understood that the present circuits may be coupled to peripheral electrodes 100b, 100c of spark head 22a to generate sparks across the spark gaps defined with common electrode 22a, as shown in FIG. 2A. In the embodiment shown, each circuit is configured to function similarly. For example, coil 404a is configured to collect and store a current for a short duration such that, when the circuit is broken at switch 420a, the magnetic field of the coil collapses and generates a so-called electromotive force, or EMF, that results in a rapid discharge of capacitor 424a across spark gap 412a.

The RL or Resistor-Inductance time constant of coil 404a—which may be affected by factors such as the size and inductive reactance of the coil, the resistance of the coil windings, and other factors—generally corresponds to the time it takes to overcome the resistance of the wires of the coil and the time to build up the magnetic field of the coil, followed by a discharge which is controlled again by the time it takes for the magnetic field to collapse and the energy to be released through and overcome the resistance of the circuit. This RL time constant generally determines the maximum charge-discharge cycle rate of the coil. If the charge-discharge cycle is too fast, the available current in the coil may be too low and the resulting spark impulse weak. The use of multiple coils can overcome this limitation by firing multiple coils in rapid succession for each pulse group (e.g., 204, 208 as illustrated in FIG. 3A). For example, two coils can double the practical charge-discharge rate by doubling the (combined) current and resulting spark impulse, and three (as shown) can effectively triple the effective charge-discharge rate. When using multiple spark gaps, timing can be very important to proper generation of spark impulses and resulting liquid vaporization and shock-waves. As such, a controller (e.g., microcontroller, processer, FPGA, and/or the like) may be coupled to each of control points 428a, 428b, 428c to control the timing of the opening of switches 420a, 420b, 420c and resulting discharge of capacitors 424a, 424b, 424c and generation of shockwaves.

Figure 6:
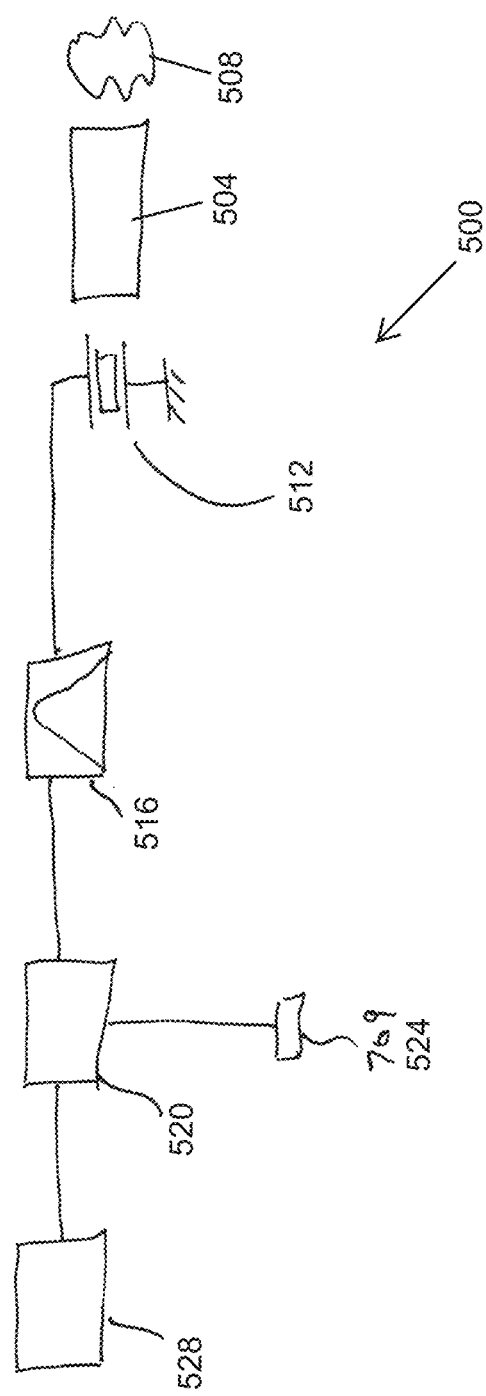
FIG. 6 depicts a block diagram of an embodiment of a radio-frequency (RF) powered acoustic ablation system.

FIG. 6 depicts a block diagram of an embodiment 500 of a radio-frequency (RF) powered acoustic shockwave generation system. In the embodiment shown, system 500 comprises a nonlinear medium 504 (e.g., as in acoustic-delay chamber 58 or nonlinear member described above) that provides an acoustic path to from a transducer 508 to target tissue 512 to produce practical harmonic or acoustic energy (e.g., shockwaves). In the embodiment shown, transducer 508 is powered and controlled through bandpass filter and tuner 516, RF power amplifier 520, and control switch 524. The system is configured such that actuation of switch 524 activates a pulse generator 528 to produce timed RF pulses that drive amplifier 520 in a predetermined fashion. A typical driving waveform, for example, may comprise a sine wave burst (e.g., multiple sine waves in rapid succession). For example, in some embodiments, a typical burst may have a burst length of 10 milliseconds and comprise sine waves having a period duration of 0.1 (frequency of 100 MHz) to more than 2 microseconds (frequency of 50 kHz).

Embodiments of the present methods comprise positioning an embodiment of the present apparatuses (e.g., 10, 38, 38a, 500) adjacent to a region of a patient comprising target cells (e.g., tissue 74); and activating the spark generation (e.g., capacitive/inductive coil) system (e.g., 26, 400) to propagate shockwaves to the target cells. In some embodiments, the region is viewed through a window (e.g., 82, 82a) while positioning the apparatus and/or while the shockwaves are generated and delivered to the region. Some embodiments further comprise coupling a removable spark head or module (e.g., 22a, 22b) to a housing of the apparatus prior to activating the pulse-generation system.

Experimental Results

Figure 7A:
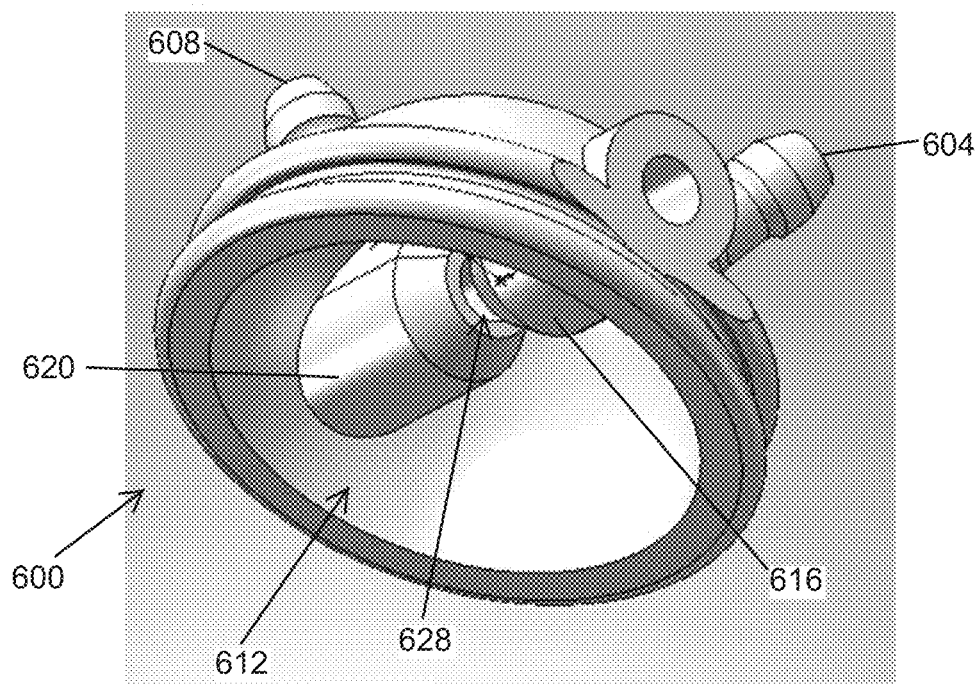
FIGS. 7A-7B depict perspective and cross-sectional views of a first prototyped spark chamber housing.
Figure 7B:
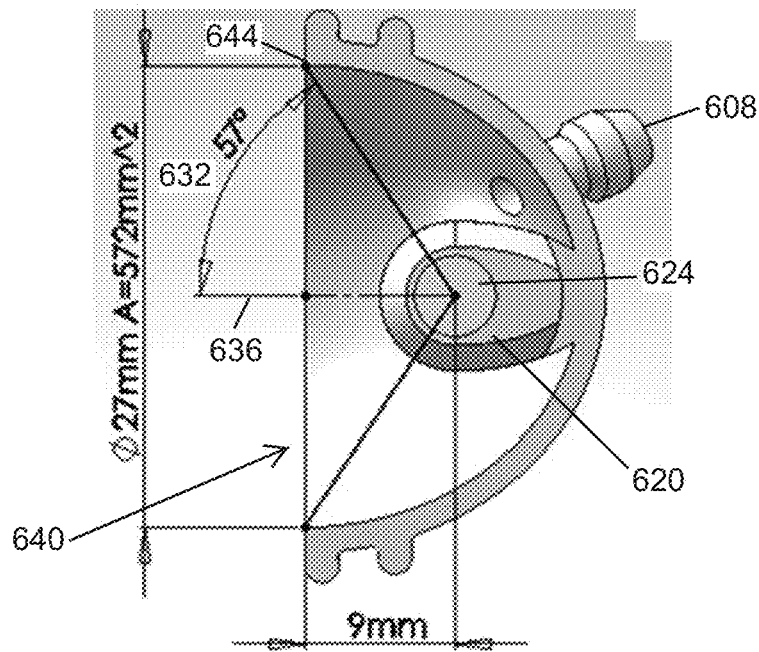
Figure 8:
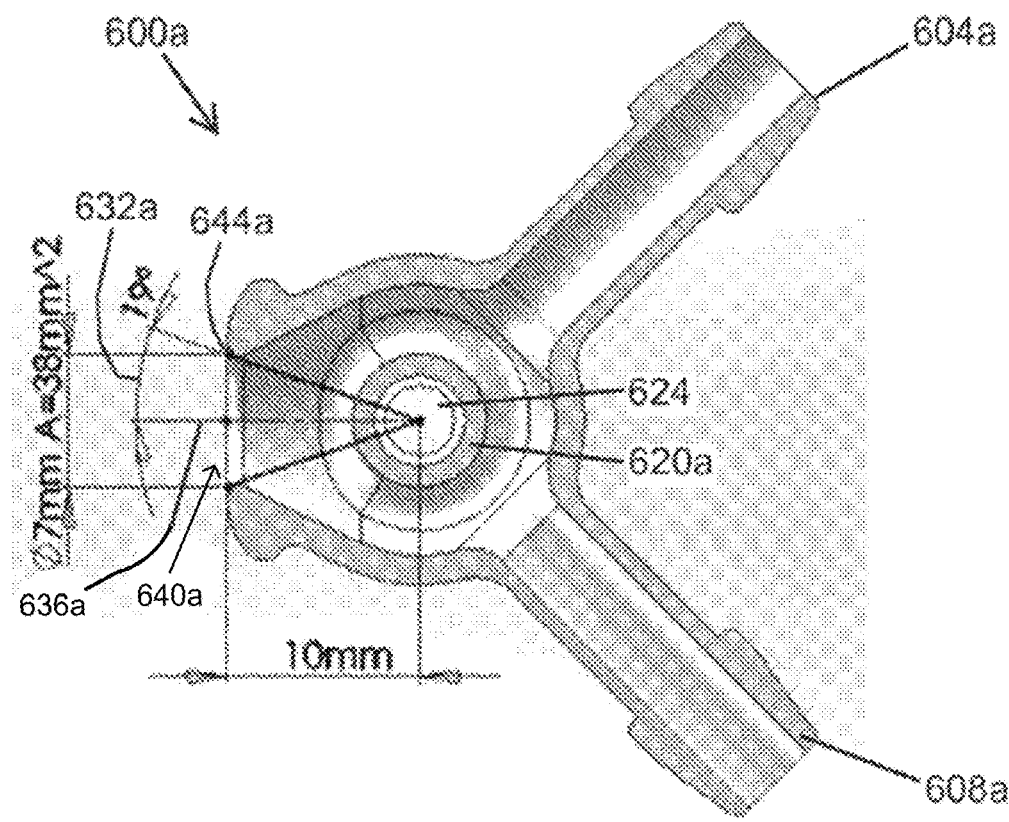
FIG. 8 depicts a cross-sectional view of a second protoyped embodiment of spark chamber housing.

Experiments were conducted on tattooed skin samples obtained from deceased primates to observe effects of EH-generated shock waves on tattooed skin. FIGS. 7A-7B and 8 depict two different prototype spark chamber housings. The embodiment of FIGS. 7A-7B depict a first embodiment 600 of a spark chamber housing that was used in the described experiments. Housing 600 is similar in some respects to the portion of housing 14a that defines head 46a of probe 38a. For example, housing 600 includes fittings 604, 608 to permit liquid to be circulated through spark chamber 612. In the embodiment shown, housing 600 includes electrode supports 616 and 620 through which electrodes 624 can be inserted to define a spark gap 628 (e.g., of 0.127 millimeters or 0.005 inches in the experiments described below). However, housing 600 has an elliptical inner surface shaped to reflect the shockwaves that initially travel backwards from the spark gap into the wall. Doing so has the advantage of producing, for each shockwave generated at the spark gap, a first or primary shockwave that propagates from the spark gap to outlet 640, followed by a secondary shock wave that propagates first to the elliptical inner wall and is then reflected back to outlet 640.

In this embodiment, supports 616 and 620 are not aligned with (rotated approximately 30 degrees around chamber 612 relative to) fittings 604, 608. In the embodiment shown, housing 600 has a hemispherical shape and electrodes 624 are positioned such that an angle 632 between a central axis 636 through the center of shockwave outlet 640 and a perimeter 644 of chamber 612 is about 57 degrees. Other embodiments can be configured to limit this angular sweep and thereby direct the sound waves and/or shockwaves through a smaller outlet. For example, FIG. 8 depicts a cross-sectional view of a second embodiment 600a of a spark chamber housing. Housing 600a is similar to housing 600, with the exception that fittings 604a, 608a are rotated 90 degrees relative to supports 616a, 620a. Housing 600a also differs in that chamber 612a includes a hemispherical rear or proximal portion and a frusto-conical forward or distal portion. In this embodiment, electrodes 624a are positioned such that such that an angle 632a between a central axis 636a through the center of shockwave outlet 640a and a perimeter 644a of chamber 612a is about 19 degrees.

Figure 9:
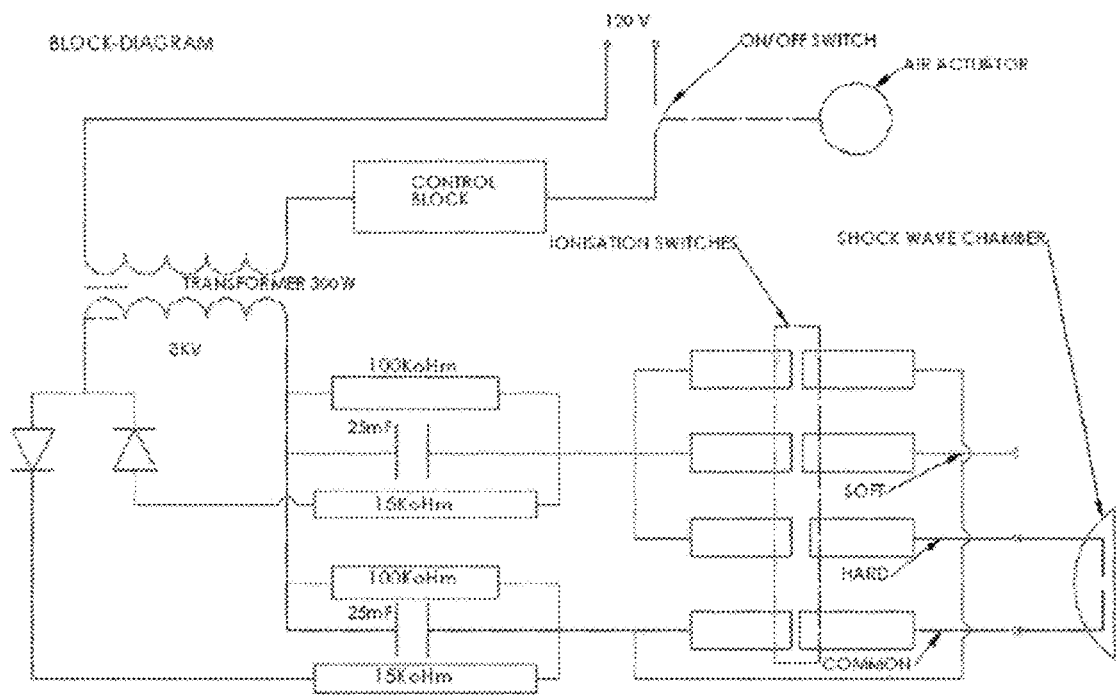
FIG. 9 depicts a schematic diagram of an electric circuit for a protyped pulse-generation system.

FIG. 9 depicts a schematic diagram of an electric circuit for a protyped pulse-generation system used with the spark chamber housing of FIGS. 7A-7B in the present experimental procedures. The schematic includes symbols known in the art, and is configured to achieve pulse-generation functionality similar to that described above. The depicted circuit is capable of operating in the relaxation discharge mode with embodiments of the present shockwave heads (e.g., 46, 46a, etc.). As shown, the circuit comprises a 110V alternating current (AC) power source, an on-off switch, a timer ("control block"), a step-up transformer that has a 3 kV or 3000V secondary voltage. The secondary AC voltage is rectified by a pair of high voltage rectifiers in full wave configuration. These rectifiers charge a pair of oppositely polarized 25 mF capacitors that are each protected by a pair of resistors (100 kΩ and 25 kΩ) in parallel, all of which together temporarily store the high-voltage energy. When the impedance of the shockwave chamber is low and the voltage charge is high, a discharge begins, aided by ionization switches, which are large spark gaps that conduct when the threshold voltage is achieved. A positive and a negative voltage flows to each of the electrodes so the potential between the electrodes can be up to about 6 kV or 6000 V. The resulting spark between the electrodes results in vaporization of a portion of the liquid into a rapidly-expanding gas bubble, which generates a shock wave. During the spark, the capacitors discharge and become ready for recharge by the transformer and rectifiers. In the experiments described below, the discharge was about 30 Hz, regulated only by the natural rate of charge and discharge—hence the term "relaxation oscillation." In other embodiments, the discharge rate can be as higher (e.g., as high as 100 Hz, such as for the multi-gap configuration of FIG. 5.

A total of 6 excised, tattooed primate skin samples were obtained, and specimens were segregated, immobilized on a substrate, and placed in a water bath. A total of 4 tattooed specimens and 4 non-tattooed specimens were segregated, with one each of the tattooed and non-tattooed specimens held as controls. Shock chamber housing 600 was placed over each of the excised specimens and voltage pulses applied to electrodes 624 at full power for various durations. Voltage of pulses were generated at a voltage of about 5-6 kV and about 10 mA, which resulted in a power level of about 50 W per pulse. For purposes of the described experiments, multiple periods of exposure were used and the results observed after the cumulative periods of exposure (e.g., cumulative total time of 10-20 minutes) as indicative of a longer period of exposure and/or a period of exposure at a greater pulse rate. The immediate results observed in the water bath showed a formation of coagulum around the edge of the samples, which was believed to indicate the flow of residual blood from the repeated shock waves. All specimens were put into formalin for histopathology. A histopathologist reported an observed disruption of cell membranes and a dispersal of the tattoo particles for tattoo pigment-containing macrophages in the treated tissue. Changes to adjacent tissue—such as thermal damage, rupture of basal cells or formation of vacuoles—were not observed. The specimen showing the most obvious disruption, which could be readily seen by an untrained eye, had the highest shock wave exposure time duration of the group. This is strongly suggestive of a threshold effect that could be further illustrated as power and/or time are increased.

Methods

Examples of maladies and/or conditions that involve particles agglomerated in cellular structures include cancer, crystalline micro-particles in the musculoskeletal system, or removal of tattoos. These are merely no limiting exemplary conditions that can be treated or addressed by rupturing or destruction of cells containing particle agglomerates. In some embodiments, destruction of the cells containing particle agglomeration may be caused by nonthermal cell membrane degradation of the specific cells secondary to nonlinear processes accompanying propagation of high frequency shock waves, as discussed above.

Some general embodiments of the present methods comprise: delivering a plurality of electro-hydraulically generated (e.g., via one or more of the present apparatuses) shock waves to at least one cellular structure comprising at least one region of heterogeneity until the at least one cellular structure ruptures. In some embodiments, the shock waves are delivered for no more than 30 minutes in a 24-hour period. In some embodiments, the shock waves are delivered for no more than 20 minutes in a 24-hour period. In some embodiments, between 200 and 5000 shockwaves are delivered in between 30 seconds and 20 minutes at each of a plurality of positions of a shockwave outlet.

A. Tattoos

Tattoos are essentially phagocytosing cells such as fibroblast cells, macrophages, and the like that contain agglomerates of ink particles. Because the captured ink particles are denser than the biological structures of the cells, tattoos or cells containing ink particles have a large difference in elasticity in its structure. When subject to shock waves, the cells containing ink particles are subject to greater mechanical strain as compared to other cells that do not contain dense particles. Shock waves can be configured to be delivered at an optimal frequency and amplitude to accelerate the ink particles sufficiently to rupture the particular cells while leaving intact fibroblast cells that do not have the particular elasticity difference. The details of tattoos and biological process of removal of released from cells are discussed further below.

Tattoo inks and dyes were historically derived from substances found in nature and generally include a heterogeneous suspension of pigmented particles and other impurities. One example is India ink, which includes a suspension of carbon particles in a liquid such as water. Tattoos are generally produced by applying tattoo ink into the dermis, where the ink generally remains substantially permanently. This technique introduces the pigment suspension through the skin by an alternating pressure-suction action caused by the elasticity of the skin in combination with the up-and-down movement of a tattoo needle. Water and other carriers for the pigment introduced into the skin diffuse through the tissues and are absorbed. For the most part, 20%-50% of the pigment is disseminated into the body. However, the remaining portion of the insoluble pigment particles are deposited in the dermis where placed. In tattooed skin, pigment particles generally are phagocytized by cells resulting in pigment agglomerates in the cytoplasm of the cells (i.e., in the membrane-bound structures known as secondary lysosomes). Resulting pigment agglomerates ("particle agglomerates") may range up to a few micrometers in diameter. Once the skin has healed, the pigment particles remain in the interstitial space of the skin tissue within the cells. Tattoo inks generally resist elimination due to the cells immobility due to the relatively large amount of insoluble pigment particles in the cells. A tattoo may fade over time, but will generally remain through the life of the tattooed person.

Tattoo inks typically comprise aluminum (87% of the pigments), oxygen (73% of the pigments), titanium (67% of the pigments), and carbon (67% of the pigments). The relative contributions of elements to the tattoo ink compositions were highly variable between different compounds. At least one study has determined the particle size for three commercial tattoo inks as shown in Table 1:

TABLE 1

Tattoo Pigment Particle Size

| Color | Mean Diameter | Std deviation |
|---|---|---|
| Viper Red | 341 nm | 189 nm |
| Agent Orange | 228 nm | 108 nm |
| Hello yellow | 287 nm | 153 nm |

B. Tattoo Removal

In conventional tattooing (decorative, cosmetic, and reconstructive), once the pigment or dye has been administered into the dermis to form a tattoo, the pigment or dye generally remains permanently in place, as discussed above.

Despite the general permanency of tattoos, individuals may wish to change will remove tattoos for a variety of reasons. For example, over time people may have a change of heart (or mind), and may desire to remove or change the design of a decorative tattoo. By way of another example, an individual with cosmetic tattooing, such as eyeliners, eyebrows, or lip coloring, may wish to change the color or area tattooed as fashion changes. Unfortunately, there is currently no simple and successful way to remove tattoos. Currently, methods of removing traditional tattoos (e.g., pigment-containing skin) may include salabrasion, cryosurgery, surgical excision, and CO2-laser. These methods may require invasive procedures associated with potential complications, such as infections, and usually results in conspicuous scarring. More recently, the use of Q-switched lasers has gained wide acceptance for the removal of tattoos. By restricting pulse duration, ink particles generally reach very high temperatures resulting in the destruction of the tattoo ink pigment-containing cells with relatively minimal damage to adjacent normal skin. This significantly decreases the scarring that often results after nonselective tattoo removal methods, such as dermabrasion or treatment with carbon dioxide laser. The mechanisms of tattoo removal by Q-switch laser radiation may still be poorly understood. It is thought that Q-switch laser allow for more specific removal of tattoos by the mechanisms of selective photothermolysis and thermokinetic selectivity. Specifically, it is thought that the pigment particles in cells are able to absorb the laser light causing heating of the particles resulting thermal destruction of the cells containing said particles. The destruction of these cells results in the release of particles which can then be removed from the tissue through normal absorptive processes.

While the Q-switch laser may be better than some alternatives for the removal of tattoos, it is not perfect. Some tattoos are resistant to all laser therapies despite the predicted high particle temperatures achieved through selective photothermolysis. Reasons cited for failure of some tattoos to clear include the absorption spectrum of the pigment, the depth of pigment, and structural properties of some inks Adverse effects following laser tattoo treatment with the Q-switched ruby laser may include textural changes, scarring, and/or pigmentary alteration. Transient hypopigmentation and textural changes have been reported in up to 50 and 12%, respectively, of patients treated with the Q-switched alexandrite laser. Hyperpigmentation and textural changes are infrequent adverse effects of the Q-switched Nd:YAG laser and the incidence of hypopigmentary changes are generally lower than with the ruby laser. The development of localized and generalized allergic reactions is also impossible (even if unusual) complication of tattoo removal with the Q-switched ruby and Nd:YAG lasers. Additionally, laser treatment may be painful, such that use of a local injection with lidocaine or topical anesthesia cream typically is used prior to laser treatment. Finally, laser removal generally requires multiple treatment sessions (e.g., 5 to 20) and may require expensive equipment for maximal elimination. Typically, since many wavelengths are needed to treat multicolored tattoos, not one laser system can be used alone to remove all the available inks and combination of inks. Even with multiple treatments, laser therapy may only be able to eliminate 50-70% of the tattoo pigment, resulting in a residual smudge.

Some embodiments of the present methods comprise: directing electro-hydraulically generated shock waves (e.g., from an embodiment of the present apparatuses) to cells of a patient; where the shock waves are configured to cause particles to rupture one or more of the cells. Some embodiments comprise: providing an embodiment of the present apparatuses; actuating apparatus to former shockwaves configured to cause particles within a patient to rupture one or more cells of the patient; and directing the shockwaves to cells of a patient such that the shockwaves cause particles to rupture one or more of the cells (e.g., such as by degradation of the cell wall or membrane). In some embodiments, the one or more shockwaves are configured to have substantially no lasting effect on cells in the absence of particles (e.g., configured to cause substantially no permanent or lasting damage to cells that are not close enough to particles to be damaged by the particles in the presence of the shockwaves).

Some embodiments of the present methods comprise focusing the one or more shockwaves a specific region of tissue that comprises the cells. In some embodiments the region of tissue at which the one or more shockwaves is focused is a depth beneath the patient's skin. The shockwaves can be focused by any of a variety of mechanisms. For example, a surface of the present apparatuses that is configured to contact a patient during use (e.g., of outlet member 70a) may be shaped (e.g., convex) to focus or shaped (e.g., convex) to disperse shockwaves, such as, for example, to narrow the area to which shockwaves are directed or expand the area to which shockwaves are directed. Focusing the shockwaves may result in higher pressures at targeted cells, such as, for example, pressures of 10 MPa, 15-25 MPa, or greater. In some embodiments, the convex outer shape is configured to tension a portion of a patient's skin as the outlet member is pressed against the skin.

Some embodiments of the present methods further comprise: identifying target cells of the patient to be ruptured (e.g., prior to directing the one or more shockwaves to the target cells). In various embodiments, the target cells can comprise any of a variety of target cells, such as, for example, target cells comprising a condition or malady involving cellular particle agglomerates. For example, the target cells may comprise: a tattoo, musculoskeletal cells comprising crystalline micro-particles, hair follicles that contain keratin protein, dental follicles that contain enamel, cancer cells, and/or the like. By way of another example, target cells may comprise one or more skin maladies selected from the group consisting of: blackheads, cysts, pustules, papules, and whiteheads.

In some embodiments, the particles can comprise non-natural particles. One example of non-natural particles includes tattoo pigment particles, such as are commonly disposed in the human dermis to create a tattoo. In some embodiments, the pigments can comprise an element with anatomic number of less than 82. In some embodiments, the particles can comprise any one or combination of: gold, titanium dioxide, iron oxide, carbon, and/or gold. In some embodiments, the particles have a mean diameter of less than 1000 nm (e.g., less than 500 nm and/or less than 100 nm).

Figure 10:
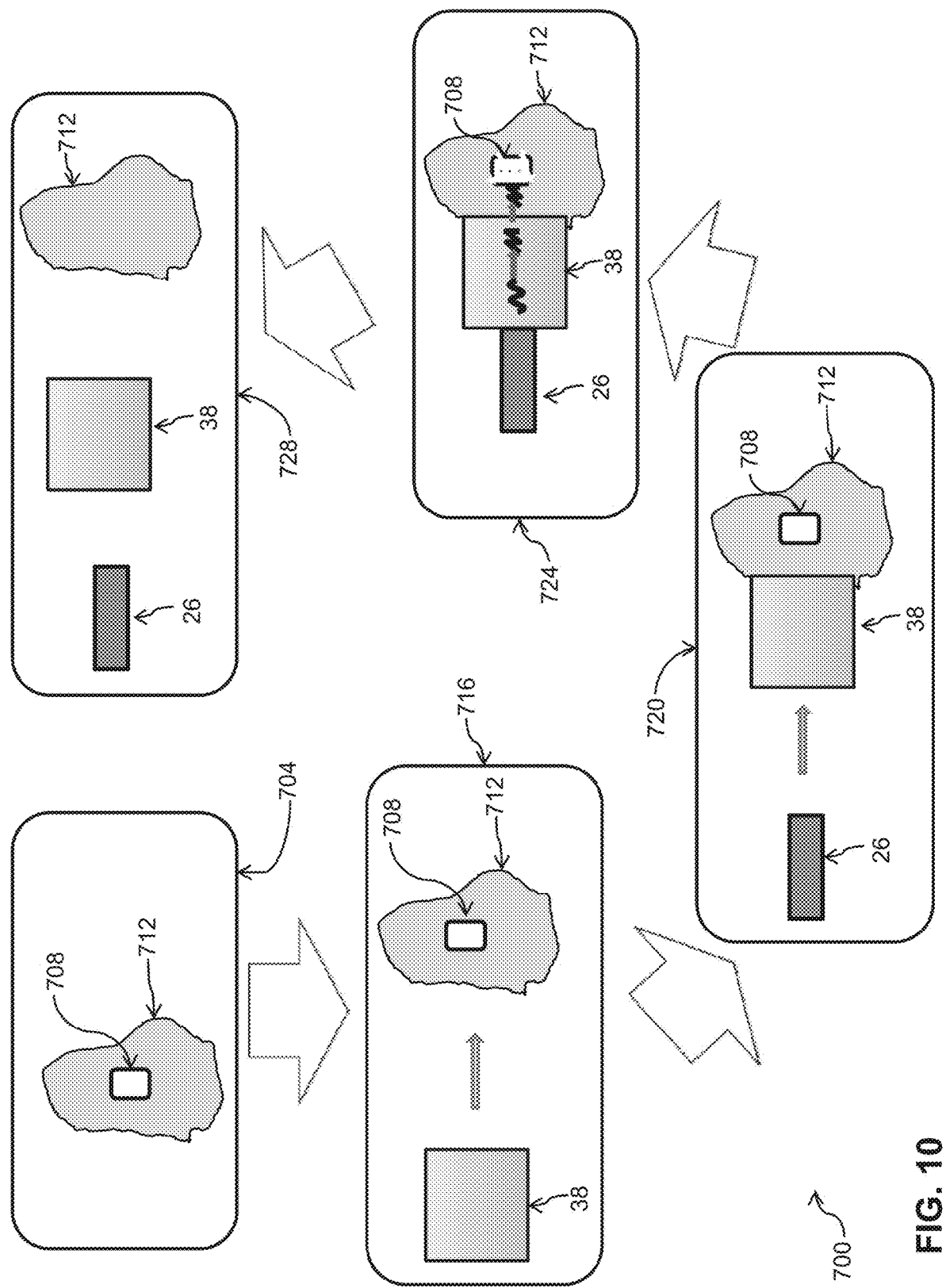
FIG. 10 depicts a conceptual flowchart of one embodiment of the present methods.

FIG. 10 illustrates one embodiment of a method 700 of using apparatus 10 to direct shockwaves to target tissue. In the embodiment shown, method 700 comprises a step 704 in which target cells 708 of a patient's tissue 712 are identified for treatment. For example, tissue 712 can comprise skin tissue, and/or target cells 708 can comprise cells containing tattoo pigment within or near skin tissue. In the embodiment shown, method 700 also comprises a step 716 in which a probe or handpiece 38 is disposed adjacent tissue 712 and/or tissue 716, such that shockwaves originating in probe 38 can be directed toward the target cells 708. In the embodiment shown, method 700 also comprises a step 720 in which a pulse-generation system 26 is coupled to probe 38. In the embodiment shown, method 700 also comprises a step 724 in which pulse-generation system 26 is activated to generate sparks across electrodes within probe 38 to generate shockwaves in probe 38 for delivery to target cells 708, as shown. In the embodiment shown, method 700 also comprises an optional step 728 in which pulse-generation system 26 is de-coupled from probe 38, and probe 38 is removed from or moved relative to tissue 712. In the embodiment shown, target cells 708 are omitted from step 728, representing their destruction. Other embodiments of the present methods may comprise some or all of the steps illustrated in FIG. 10.

C. Methods of Removing Tissue Markings

In some embodiments of the present methods of diminishing tissue markings (e.g., tattoos) caused by pigments in dermis tissue involve the use of one of the present apparatuses. In such methods, high-frequency shockwaves are transmitted to and into a patient's skin, such that when the shock waves generated from the apparatus of the present disclosure reach the dermal cells and vibrate or accelerate the intradermal particles, these particles experience movement relative cell membranes that can lead to fatigue degradation and rupturing of cells, thereby releasing the pigment particles. Released particles can then be removed from the surrounding tissue through normal absorptive processes of the patient's body. In some embodiments, one of the present apparatuses can be disposed adjacent to, and/or such that the shock waves from the apparatus are directed to the tissue site having the tattoo, other tissue markings, or other cellular structures containing particle agglomerates. To cause particle alteration (e.g., cell degradation sufficient to release particles for absorption), the shock waves can be delivered to a specific area for a period of time long enough to rupture cells containing and/or adjacent to the pigment particles such that the pigment particles are released. In some embodiments the present apparatuses have a focus or effective area that may be relatively smaller than a tattoo, such that the apparatus may be periodically and are sequentially focused are directed at different areas of a tattoo to cause a reduction in perceptible pigments over the entire area of the tattoo. For instance, the parameters of the embodiments of the apparatus disclosed here can be modified to achieve the desire number of shocks delivered to a particular site in a desired amount of time. For instance, in one embodiment, shock waves are produced from acoustic waves with frequency of at least 1 MHz according to aspects of the present disclosure and exposed to a particular treatment site for the appropriate period of time to deliver at least about 100, 200, 300, 400, 500, or 1000 shock waves to the treatment site. The shock waves can be delivered all at once or through intervals (e.g., bursts) of shock waves (such as 5, 10, 15, 20, 25, 30, 40, 50, etc. shock waves at a time). The appropriate interval and time between the interval can be modified and/or determined to achieve the desired effect at the treatment site, e.g., rupture of the targeted cellular structures. It is understood that if acoustic waves with higher frequency are used, such as 2 MHz, 3 MHz, 4 MHz, or 5 MHz, the treatment time can be adjusted, likely shorter exposure time, to achieve the desired amount of shock waves delivered to the treatment area.

As will be appreciated by those of ordinary skill in the art, in embodiments of the present methods for removing tattoos, the particles affected by the shock waves can comprise tattoo pigment (particles), such as may, for example, be at least partially disposed between and/or within skin cells of the patient. Such pigment particles may, for example, include at least one or combination of any of the following: titanium, aluminum, silica, copper, chromium, iron, carbon, or oxygen.

The use of high frequency shock waves to remove or reduce skin markings has many advantages over the use of lasers. For example, laser treatments for tattoo removal may be very painful. In contrast, high-frequency shockwaves (e.g., ultrasound shockwaves) can be configured and/or applied such that tattoos or other skin markings may be removed or diminished with little if any pain to the patient, especially, for example, where the shock waves are targeted or otherwise configured to degrade only cells that contain tattoo pigments. By way of another example, laser light directed at tissue has been found to cause damage to or destruction of surrounding tissues; whereas high-frequency shock waves may be applied so as to cause little damage or destruction of surrounding tissues (e.g., because non-tattooed surrounding tissues generally lack tattoo pigment or other particles that might otherwise interact with neighboring cells to cause sell degradation). Finally, laser tattoo removal often requires multiple treatment sessions (e.g., 5-20 sessions) for maximal tattoo elimination, and/or often requires the use of expensive equipment. Additionally, since many wavelengths a laser light may be needed to remove multicolored tattoos, multiple laser systems may be needed to remove the variety of available inks and/or combinations of available inks. As a result, the overall cost of laser tattoo removal may be prohibitively expensive. Even with multiple treatments, laser therapy may be limited to eliminating only 50 to 70% of tattoo pigment, and may leave a residual "smudge." In contrast, high-frequency shockwaves is not dependent upon the color of tattoo pigments such that therapeutic application of high-frequency shockwaves does not require different apparatuses for different colors of pigment, and such that high-frequency shockwaves may be applied to a relatively large area (e.g., the entire area of a tattoo), thereby reducing the number of treatment sessions required to achieve a level of tattoo removal or reduction that is acceptable to the patient (e.g., 30, 40, 50, 60, 70, 80, 90, 95, or more percent reduction in the perceivable pigment in the patient's skin).

In some embodiments, the present methods include the application of high-frequency shockwaves (e.g. with one or more of the present apparatuses) and the application of laser light. For example, some embodiments of the present methods further comprise directing a beam of light from a Q-switched laser at the target cells (e.g., tattooed skin). In some embodiments, directing one or more shockwaves and directing the beam of light are performed in alternating sequence.

In some embodiments, the present methods include delivering one or more chemical or biological agents (e.g., configured to aid in the removal of tissue markings such as tattoos) to a position at or near the target cells before, after, and/or simultaneously with directing the one or more shockwaves to the target cells. For example, some embodiments of the present methods further comprise applying a chemical or biological agent to the skin (e.g., before, after, and/or simultaneously with directing one or more shockwaves and/or a beam of laser light at the skin). Examples of chemical or biological agents include: chelators (e.g., ethylenediaminetetraacetic acid (EDTA)); immune modulators (e.g., Imiquimod [5]); combinations thereof; and/or other suitable chemical in or biological agents. In various embodiments, chemical in or biological agents to be delivered transdermally and/or systemically (e.g., the injection) to the target cells (e.g., may be applied topically to tattooed skin).

Some embodiments of the present methods of tattoo removal include multiple applications of shockwaves to tattooed skin tissue (e.g., for a duration of at least 1 second (e.g., 10 seconds, or more), once per week for 6 or more weeks).

D. Method of Treating Additional Maladies and Conditions

In addition to tattoo removal, embodiments of the present methods may include the application of high-frequency shockwaves to treat a variety of maladies under conditions caused by and/or including symptoms of cellular particle agglomerates and/or particles disposed in intracellular spaces and/or interstitial spaces. For example, such maladies and/or conditions may include: crystal joint, ligament, tendon and muscle disease, and/or dermatological maladies involving particle agglomerates including acne, age spots, etc. Additionally, embodiments of the present methods may include the application of high-frequency shockwaves after delivering nanoparticles to a region of the patient that includes the target cells. For example, in some embodiments, nanoparticles (e.g., gold nanoparticles) are delivered to a patient's bloodstream intravenously and permitted to travel to a region of the patient that includes the target cells (e.g. a cancerous tumor), such that high-frequency shockwaves can be directed to the target region to cause the nanoparticles to interact with and rupture the target cells.

Further, embodiments of the present apparatuses (e.g., apparatus 10) can be used for wrinkle reduction. For example, some embodiments of the present methods of generating therapeutic shock waves, comprise: providing any of the present apparatuses (e.g., apparatus 10); and actuating the apparatus to generate one or more shock waves. Some embodiments further comprise: disposing the apparatus (e.g., outlet end 34 of housing 18) adjacent tissue of a patient such that at least one shock wave enters the tissue. In some embodiments, the tissue comprises skin tissue on the face of the patient.

In embodiments of the present methods that include directing particles (e.g., micro-particles and/or nanoparticles) to a position at or near the target cells (prior to directing shockwaves to the cells), the particles can comprise: silk, silk fibron, carbon nanotubes, liposomes, and/or gold nanoshells. For example, in some embodiments, directing the particles can comprises injecting into the patient a fluid suspension that includes the particles. Include suspension may, for example, comprise saline and/or hyaluronic acid.

Deposition of crystals and other miscellaneous crystals in articular and particular tissues can result in a number of disease states. For example, monosodium urate monohydrate (MSUM) deposition in a joint may results in gout. As another example, calcium pyrophosphate dehydrate (CPPD) in joint tissues and fluids may result in a number of disease conditions, such as, for example, chondrocalcinosis (i.e., presence of calcium-containing crystals detected as radiodensities in articular cartilage). By way of further example, hydroxyapatite (HA) crystal deposition may result in calcific tendonitis and perarthritis. In some embodiments of the present methods, the particles may comprise natural particles (e.g., particles naturally occurring within the body), such as, for example, crystalline micro-particles such as may be form and/or become disposed in the musculoskeletal system of a patient. Other examples of natural particles they may be treated and/or disbursed in the present methods include: urate crystals, calcium-containing crystals, and/or hyroxyapatite crystals.

In embodiments of the present methods for treatment of acne or other skin-based conditions, the particles may comprise dirt and/or debris that is disposed in one or more pores of the patient's skin, and/or may comprise keratin protein disposed of the patient's skin. In embodiments of the present methods of treating (e.g., pathological) conditions associated with bone and musculoskeletal environments and soft tissues by applying shockwaves can induce localized trauma and cellular apoptosis (including micro-fractures), or may induce osteoblastic responses such as cellular recruitment, stimulate formation of molecular bone, cartilage, tendon, fascia, and soft tissue morphogens and growth factors, and/or may induce vascular neoangiogenesis.

Some embodiments of the present methods of treating tumors or other maladies include multiple applications of shockwaves to targeted tissue (e.g., a tumor, an area of skin with acne or other conditions, etc.), such as, for example, for a duration of at least (e.g., 10 seconds, or more), once per week for 6 or more weeks.

The above specification and examples provide a description of the structure and use of exemplary embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the present devices are not intended to be limited to the particular forms disclosed. Rather, they include all modifications and alternatives falling within the scope of the claims, and embodiments other than the one shown may include some or all of the features of the depicted embodiment. For example, components may be combined as a unitary structure. Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

REFERENCES

[1] Burov, V. A., Nonlinear ultrasound: breakdown of microscopic biological structures and nonthermal impact on malignant tumor. *Doklady Biochemistry and Biophysics Vol.* 383, pp. 101-104 (2002).
[2] Delius, M., Jordan, M., & et al. (1988). Biological effects of shock waves: Kidney Haemorrhage by shock waves in dogs—administration rate dependence. *Ultrasound in Med. & Biol.,* 14(8), 689-694.
[3] Fernandez, P. (15 May 2006). A master relation defines the nonlinear viscoelasticity of single fibroblasts. *Biophysical journal, Vol.* 90, Issue 10, 3796-3805.
[4] Freund, J. B., Colonius, T., & Evan, A. P. (2007). A cumulative shear mechanism for tissue damage initiation in shock-wave lithotripsy. *Ultrasound in Med & Biol,* 33(9), 1495-1503.
[5] Gillitzer, R., & et al. (2009). Low-frequency extracorporeal shock wave lithotripsy improves renal pelvic stone disintegration in a pig model. *BJU Int,* 176, 1284-1288.
[6] Kasza, K. E. (2007). The cell as a material. *Current Opinion in Cell Biology* 2007, 19:101-107.
[7] Madbouly, K., & et al. (2005). Slow versus fast shock wave lithotripsy rate for urolithiasis: a prospective randomized study. *The Journal of urology,* 173, 127-130.

The invention claimed is:
1. An apparatus comprising:
a housing defining a chamber and a shockwave outlet, the chamber configured to be filled with a liquid; and
a plurality of electrodes disposed in the chamber and configured to be coupled to a pulse-generation system, the plurality of electrodes including a first electrode and a second electrode, the first electrode and the second electrode defining a first spark gap;
a hinge coupled to the second electrode, the hinge configured to enable a change in a physical position of the second electrode with respect to the first electrode;
wherein, when the plurality of electrodes is coupled to the pulse-generation system and when the chamber is filled with the liquid:
the plurality of electrodes is configured to receive voltage pulses from the pulse-generation system at a rate of between 10 Hz and 5 MHz such that portions of the liquid are vaporized to generate therapeutic shockwaves that propagate through the liquid and the shockwave outlet; and
the first electrode is configured to receive a first voltage pulse of the voltage pulses and to discharge a first spark across the first spark gap to the second electrode.

2. The apparatus of claim 1, further comprising a plurality of connectors configured to be removably coupled to the pulse-generation system, the plurality of connectors including a first connector electrically coupled to the first electrode and a second connector electrically coupled to the second electrode.

3. The apparatus of claim 1, further comprising:
a member coupled to the hinge;
wherein the second electrode is coupled to the member such that the second electrode is configured to be displaced toward or away from the first electrode while the member pivot about the hinge; and
wherein the housing further comprises two liquid connections in fluid communication with the chamber, and wherein a position of the second electrode is configured to move, responsive to discharge of the first spark, from a first position within the chamber to a second position within the chamber.

4. The apparatus of claim 3, further comprising:
a liquid reservoir; and
a pump configured to circulate the liquid from the reservoir to the chamber of the housing via the two liquid connections.

5. The apparatus of claim 1, further comprising the pulse-generation system, and wherein the pulse-generation system comprises:
a first capacitive/inductive coil circuit comprising:
an induction coil configured to be discharged to apply at least some of the voltage pulses;
a switch; and
a capacitor;
wherein the capacitor and the switch are coupled in parallel between the induction coil and a current source.

6. The apparatus of claim 5, wherein the pulse-generation system further comprises:
a second capacitive/inductive coil circuit; and
a timer configured to coordinate the discharge of the induction coils of each of the first and second capacitive/inductive coil circuits.

7. The apparatus of claim 1, wherein the plurality of electrodes further includes a third electrode, and wherein a second spark gap is defined by the second electrode and the third electrode.

8. The apparatus of claim 1, further comprising:
a translucent or transparent window incorporated in the housing and positioned such that a portion of the chamber is intermediate the translucent or transparent window and the shockwave outlet;
wherein the translucent or transparent window is configured to enable a first line-of-sight through the translucent or transparent window into the chamber of the housing to view, via the chamber and the shockwave outlet, a region of a patient comprising target cells; and
wherein the plurality of electrodes is positioned within the chamber such that the plurality of electrodes are not disposed along the first line-of-sight extending through the translucent or transparent window.

9. The apparatus of claim 8, further comprising:
an optical shield disposed within the chamber and positioned between the window and the plurality of electrodes.

10. The apparatus of claim 8, further comprising:
an acoustic mirror configured to reflect shockwaves from the plurality of electrodes to the shockwave outlet.

11. The apparatus of claim 10, wherein the acoustic mirror comprises glass.

12. An apparatus comprising:
a probe including a handle portion;
a liquid; and
a spark module configured to be removably coupled to the probe, the spark module comprising:
   a sidewall defining a spark chamber associated with a shockwave outlet, the spark chamber configured to be filled with the liquid;
   a probe connector coupled to the sidewall and configured to be electrically coupled to the probe via the module connector; and
   a plurality of electrodes disposed in the spark chamber, the plurality of electrodes comprising a first electrode and a second electrode that define a first spark gap and at least one electrode of the plurality of electrodes is electrically coupled to the probe connector;
   wherein the spark module is removable from the probe as a single unit that includes the sidewall, the probe connector, and the plurality of electrodes;
a pulse-generation system coupled to the probe and configured to generate voltage pulses; and
wherein, when the spark chamber is filled with the liquid and the spark module is coupled to the pulse-generation system via the probe, the plurality of electrodes is configured to receive the voltage pulses from the pulse-generation system such that portions of the liquid are vaporized to generate therapeutic shockwaves that propagate through the liquid and the shockwave outlet.

13. The apparatus of claim 12, wherein:
the plurality of electrodes is removably disposed in the spark chamber; and
the handle portion comprises a manually operated switch configured to be electrically coupled to the pulse-generation system.

14. The apparatus of claim 12, wherein:
the sidewall comprises a polymer, and
the spark module further comprises:
   an acoustically permeable cap configured to be removably coupled to the sidewall;
   two liquid connections in fluid communication with the spark chamber; and
   a hinge or a flexible beam coupled to a first electrode of the plurality of electrodes and configured to enable a change in a physical position of the first electrode with respect to a second electrode of the plurality of electrodes; and
the handle portion of the probe comprises:
   two conduits that extend from a first end of the handle portion to a second end of the handle portion and coupled to the two liquid connections of the spark module, the two conduits configured to enable circulation of the liquid.

15. The apparatus of claim 14, wherein at least a portion of the sidewall is configured to transmit shockwaves through the liquid in the spark chamber towards the acoustically permeable cap.

16. The apparatus of claim 12, wherein:
the sidewall of the spark module comprises at least one of pins, grooves, or threads,
the probe comprises:
   at least one of corresponding grooves, pins, or threads to releasably couple the spark module to the probe,
   a high voltage connector positioned on a first end of the handle portion and coupled to the pulse-generation system,
   a plurality of electrical conductors coupled to the high voltage connector, and
   a manually operated trigger switch coupled to the handle portion, and
a position of a first electrode of the plurality of electrodes with respect to a second electrode of the plurality of electrodes is moveable from a first position within the spark chamber to a second position within the spark chamber.

17. A method comprising:
electro-hydraulically generating a plurality of first shockwaves at a frequency of between 10 Hz and 5 MHz, the plurality of first shockwaves generated using a first spark module coupled to a probe, the probe coupled to a pulse-generation system and including a handle portion and, the first spark module coupled to the probe and including a first sidewall defining a spark chamber, a plurality of electrodes disposed in the spark chamber, and a hinge coupled to a first electrode of the plurality of electrodes;
delivering at least a portion of the plurality of first shockwaves to at least one cellular structure comprising at least one region of heterogeneity such that the at least one cellular structure is ruptured responsive to delivery of the at least a portion of the plurality of first shockwaves;
changing, based on operation of the hinge, a physical position of the first electrode with respect to a second electrode of the plurality of electrodes;
after electro-hydraulically generating the plurality of first shockwaves and changing the physical position of the first electrode, decoupling the first spark module from the probe;
coupling a second spark module to the probe, the second spark module including a second sidewall and a second plurality of electrodes coupled to the second sidewall; and
electro-hydraulically generating a second plurality of shockwaves using the second spark module.

18. The method of claim 17, where the at least one region of heterogeneity comprises an effective density greater than an effective density of the at least one cellular structure.

19. The method of claim 17, further comprising varying the frequency of the first or second shockwaves.

20. The method of claim 17, wherein the at least one region of heterogeneity is disposed in an epidermis layer of a patient.

21. The method of claim 20, wherein the at least one region of heterogeneity includes cells that contain tattoo pigment particles.

22. The method of claim 17, further comprising:
identifying at least one target cellular structure to be ruptured prior to delivering at least a portion of first or second shockwaves to the at least one target cellular structure.

23. The method of claim 17, wherein electro-hydraulically generating the plurality of first or second shockwaves comprises:
receiving, at the plurality of electrodes, a first voltage pulse from the pulse-generation system via the probe, the plurality of electrodes including the first electrode, the second electrode, and a third electrode;
generating a first spark responsive to the first voltage pulse to electro-hydraulically generate a first shockwave of the plurality of first or second shockwaves;
receiving, at the plurality of electrodes, a second voltage pulse from the pulse-generation system; and generating a second spark responsive to the second voltage pulse to electro-hydraulically generate a second shockwave of the plurality of first or second shockwaves.

24. The method of claim 23, wherein the second voltage pulse is a next voltage pulse subsequent to the first voltage pulse.

25. The method of claim 23, further comprising, after the plurality of electrodes receiving the first voltage pulse and prior to the plurality of electrodes receiving the second voltage pulse, moving at least one electrode of the plurality of electrodes from a first position within the spark chamber to a second position within the spark chamber.

* * * * *